(12) United States Patent
Amemiya

(10) Patent No.: US 7,775,112 B2
(45) Date of Patent: Aug. 17, 2010

(54) METHOD OF SECTOR PROBE DRIVING AND ULTRASOUND DIAGNOSTIC APPARATUS

(75) Inventor: Shinichi Amemiya, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 827 days.

(21) Appl. No.: 10/862,718

(22) Filed: Jun. 7, 2004

(65) Prior Publication Data

US 2004/0260179 A1    Dec. 23, 2004

(30) Foreign Application Priority Data

Jun. 9, 2003    (JP) .............................. 2003-163069

(51) Int. Cl.
G01R 33/20 (2006.01)

(52) U.S. Cl. ........................................ 73/628; 600/437

(58) Field of Classification Search ................. 600/643, 600/447, 460, 444, 459, 45, 455, 449, 448, 600/443; 73/626

See application file for complete search history.

(56) References Cited

U.S. PATENT DOCUMENTS

| | | | |
|---|---|---|---|
| 5,787,889 A | 8/1998 | Edwards et al. | |
| 5,795,296 A | 8/1998 | Pathak et al. | |
| 5,844,139 A | 12/1998 | Miller et al. | |
| 5,897,501 A * | 4/1999 | Wildes et al. | 600/447 |
| 6,014,897 A * | 1/2000 | Mo | 73/628 |
| 6,089,096 A * | 7/2000 | Alexandru | 73/626 |
| 6,436,047 B1 * | 8/2002 | Ramamurthy et al. | 600/447 |
| 6,783,497 B2 * | 8/2004 | Grenon et al. | 600/459 |
| 2005/0124891 A1 * | 6/2005 | Amemiya | 600/447 |

FOREIGN PATENT DOCUMENTS

| | | |
|---|---|---|
| JP | H04-327841 | 11/1992 |
| JP | H09-084795 | 3/1997 |
| JP | A2001-238882 | 9/2001 |
| JP | A2001-292496 | 10/2001 |
| JP | A2002-224101 | 8/2002 |

OTHER PUBLICATIONS

"Medical Ultrasound Apparatus Handbook", Fig.3.59 on p. 94, Fig. 3.64 on p. 97, and Fig.3.76 on p. 102, edited by Electronic Industries Association of Japan, published by Corona Corp. for the first revision on Jan. 20, 1997.
An English Translation of a Portion of Japanese Publication No. H04-327841, Date of publication: Nov. 17, 1992.

* cited by examiner

*Primary Examiner*—Brian Casler
*Assistant Examiner*—Elmer Chao
(74) *Attorney, Agent, or Firm*—Armstrong Teasdale LLP

(57) ABSTRACT

The transmitter/receiver for a convex probe and linear probe are used to drive a sector probe. Usually, when an ultrasound diagnostic apparatus using a convex probe and linear probe uses a sector probe, it selects vibration elements of N in number, which is equal to the number of channels of the sector probe, out of vibration elements of L in number (N is smaller than L), so that the selected elements are distributed at a virtually constant pitch in the alignment of vibration elements, and turns on only high voltage switches which are connected with the selected vibration elements to implement the sector scanning with the transmitter/receiver. It becomes possible to implement the sector scanning by using the transmitter/receiver having channels less than the number of vibration elements of the sector probe.

20 Claims, 17 Drawing Sheets

METHOD OF SECTOR PROBE DRIVING AND ULTRASOUND DIAGNOSTIC APPARATUS

CROSS REFERENCE TO RELATED APPLICATIONS

This application claims the benefit of Japanese Application No. 2003-163069 filed Jun. 9, 2003.

BACKGROUND OF THE INVENTION

The present invention relates to a method of sector probe driving and an ultrasound diagnostic apparatus, and particularly to a method of sector probe driving and an ultrasound diagnostic apparatus which are capable of driving a sector probe by using the transmitter/receiver for a convex probe and linear probe.

An ultrasound diagnostic apparatus using a convex probe and linear probe is equipped with a transmitter/receiver having a 0th through 31st channels and a high voltage switch including a 0th through 127th switches, for example, with each n-th channel, where n takes 0 through 31, being connected in parallel fashion to the n-th switch, the (n+32)th switch, . . . , and the (n+96)th switch. The 0th through 127th switches are connected to the 0th through 127th vibration elements, respectively, of the convex probe and linear probe. Only the 0th through 31 st switches are turned on to drive the 0th through 31st vibration elements, and next, only the 1st through 32nd switches are turned on to drive the 1st through 32nd vibration elements, and next, only the 2nd through 33rd switches are turned on to drive the 2nd through 33rd vibration elements, and so on, so that 32 vibration elements are driven at a time in turn, thereby implementing the linear scanning or convex scanning. An ultrasound diagnostic apparatus using a sector probe is equipped with a transmitter/receiver having a 0th through 63rd channels, for example, with the 0th through 63rd channels being connected to the 0th through 63rd vibration elements, respectively, of the sector probe. The 0th through 63rd channels drive the 0th through 63rd vibration elements by being timed with different delay times, thereby implementing the sector scanning. (Refer to non-patent publication 1, for example.)

[Non-patent publication 1]

"Medical Ultrasound Apparatus Handbook", FIG. 3.59 on p. 94, FIG. 3.64 on p. 97, and FIG. 3.76 on p. 102, edited by Electronic Industries Association of Japan, published by Corona Corp. for the first revision on Jan. 20, 1997.

The transmitter/receiver for a convex probe and linear probe has a smaller number of channels than the number of vibration elements of the convex probe and linear probe, as mentioned previously. Whereas, the transmitter/receiver for a sector probe has channels larger than or equal in number to the vibration elements of the sector probe. Due to this difference, the conventional ultrasound diagnostic apparatus has a problem of incapacity for driving a sector probe by using the transmitter/receiver for a convex probe and linear probe.

Specifically, an ultrasound diagnostic apparatus intended for the diagnosis of internal medicine and superficial tissue has a transmitter/receiver of 32 channels for example and uses a convex probe and linear probe of 128 vibration elements for example. Whereas, an ultrasound diagnostic apparatus intended for the diagnosis of circulatory organs has a transmitter/receiver of 64 channels for example and uses a sector probe of 64 vibration elements for example. It has not been possible for the former ultrasound diagnostic apparatus to use the sector probe of the latter apparatus.

SUMMARY OF THE INVENTION

Accordingly, it is an object of the present invention is to provide a method of sector probe driving and an ultrasound diagnostic apparatus which are capable of driving a sector probe by using the transmitter/receiver for a convex probe and linear probe.

At a first object of invention, the present invention resides in a method of driving a sector probe having vibration elements of L in number through channels of N in number of a transmitter or receiver for a convex probe and linear probe, where L is larger than N, the method being characterized by selecting and driving vibration elements of N in number which are located at a constant pitch or virtually constant pitch in the alignment of vibration elements.

The sector probe driving method of the first object of invention selects and drives vibration elements of N in number, which is equal to the number of channels of the transmitter or receiver, located at a constant pitch or virtually constant pitch in the alignment of L vibration elements of the sector probe. The resulting ability of sector scanning enables the sector probe driving by use of the transmitter/receiver for the convex probe and linear probe. A wide distribution of vibration elements allows a large aperture.

At a second object of invention, the present invention resides in a method of driving a sector probe having vibration elements of L in number through channels of N in number of a transmitter or receiver for a convex probe and linear probe, where L is larger than N, the method being characterized by selecting and driving vibration elements of N in number which are located at the middle or nearly middle of the alignment of vibration elements.

The sector probe driving method of the second object of invention selects and drives vibration elements of N in number, which is equal to the number of channels of the transmitter or receiver, located at the middle or nearly middle of the alignment of L vibration elements of the sector probe. The resulting ability of sector scanning enables the sector probe driving by use of the transmitter/receiver for the convex probe and linear probe. A dense distribution of vibration elements suits for imaging of a shallow portion.

At a third object of invention, the present invention resides in a method of driving a sector probe having vibration elements of L in number through channels of N in number of a transmitter or receiver for a convex probe and linear probe, where L is larger than N, the method being characterized by selecting and driving vibration elements of N in number at random out of the L vibration elements.

The sector probe driving method of the third object of invention selects and drives vibration elements of N in number, which is equal to the number of channels of the transmitter or receiver, at random out of the L vibration elements of the sector probe. The resulting ability of sector scanning enables the sector probe driving by use of the transmitter/ receiver for the convex probe and linear probe. An irregular distribution of vibration elements alleviates the emergence of grating lobe.

At a fourth object of invention, the present invention resides in a method of driving a sector probe having vibration elements of L in number through channels of N in number of a transmitter or receiver for a convex probe and linear probe, where L is larger than N, the method being characterized by selecting and driving vibration elements of N/2 in number at random out of vibration elements of L/2 in number which are located on one side of the middle of the alignment of vibration elements and vibration elements of N/2 in number which are located symmetrically or nearly symmetrically to the first-selected vibration elements across the middle of the alignment of vibration elements.

The sector probe driving method of the fourth object of invention selects and drives vibration elements of N/2 in number, which is half the number of channels of the transmitter or receiver, at random out of the L/2 vibration elements which are located on one side of the middle of the alignment of vibration elements of the sector probe. The method also selects and drives vibration elements of N/2 in number which are located symmetrically or nearly symmetrically to the first-selected vibration elements across the middle of the alignment of vibration elements. The resulting ability of sector scanning enables the sector probe driving by use of the transmitter/receiver for the convex probe and linear probe. An irregular distribution of the half vibration elements alleviates the emergence of grating lobe. In addition, a virtually symmetric distribution of vibration elements to be driven simplifies the setting of delay times for sector scanning.

At a fifth object of invention, the present invention resides in a method of sector probe driving, which is derived from the above-mentioned arrangement and is characterized by raising the probability of selection of vibration elements which are located at the middle or nearly middle of the alignment of vibration elements.

A fairly dense distribution of vibration elements to be driven at the middle or nearly middle of the alignment of vibration elements, which is achieved by the sector probe driving method of the fifth object of invention, suits for imaging of a shallow portion.

At a sixth object of invention, the present invention resides in a method of sector probe driving, which is derived from the above-mentioned arrangement and is characterized by lowering the probability of selection in contiguous order of vibration elements which are located far from the middle of the alignment of vibration elements.

The sector probe driving method of the sixth object of invention has a scarce distribution of vibration elements to be driven at positions far from the middle of the alignment of vibration elements. In other words, a relatively dense element distribution nearly at the middle suits for imaging of a shallow portion.

At a seventh object of invention, the present invention resides in a method of driving a sector probe having vibration elements of L in number through channels of N in number of a transmitter or receiver for a convex probe and linear probe, where L is larger than N, the method being characterized by selecting and driving contiguous vibration elements of C in number which are located at the middle or nearly middle of the alignment of vibration elements and every b-th element among vibration elements of N-C in number which are located on both sides of the C vibration elements.

The sector probe driving method of the seventh object of invention selects and drives vibration elements of C in number which are located at the middle or nearly middle of the alignment of L vibration elements of the sector probe. The method also selects and drives every b-th element among vibration elements of N-C in number which are located on both sides of the C vibration elements. The resulting ability of sector scanning enables the sector probe driving by use of the transmitter/receiver for the convex probe and linear probe. A dense distribution of C vibration elements at the middle or nearly middle of the alignment of vibration elements suits for imaging of a shallow portion. In addition, a relatively large aperture is allowed.

At an eighth object of invention, the present invention resides in a method of sector probe driving, which is characterized by selecting one of at least two of the sector probe driving methods derived from the above-mentioned arrangement depending on at least one of the ultrasound diagnostic mode, scanning depth, scanning angle, and ultrasound frequency.

The sector probe driving method of the eighth object of invention can select one of the above-mentioned sector probe driving methods of the first through sixth object of invention which matches with the ultrasound diagnostic mode, scanning depth, scanning angle, or ultrasound frequency.

At a ninth object of invention, the present invention resides in an ultrasound diagnostic apparatus which is characterized by comprising: a transmitter or receiver having a 0th through (N−1)th channels; a high voltage switch including a 0th through (M−1)th switches, where M has a value of N multiplied by a natural number k of 2 or larger; and a sector probe having vibration elements of L in number, where N<L≦M, which are aligned in the order from the 0th through (L−1)th vibration elements, each n-th channel, where n takes 0 through N−1, being connected in parallel fashion to the n-th switch, the switch, the (n+N)th switch, . . . , and the (n+(k−1)N)th switch, the 0th through (L−1)th vibration elements of the sector probe being connected to the 0th through (L−1)th switches, respectively, each set of a m-th through (m+N−1)th switches, where m takes 0, N, . . . , (k−1)N, being united to be a (m/N)th switch group. The ultrasound diagnostic apparatus further comprises a switch control means which selects two switch groups in which all switches are connected with vibration elements, turns on only odd-numbered switches for one switch group, turns on only even-numbered switches for another switch group, and turns off switches which are of other switch groups and connected with vibration elements.

The ultrasound diagnostic apparatus of the ninth object of invention selects consecutive vibration elements of 2N in number out of the L vibration elements, and is capable of implementing the sector probe driving method of the first object of invention for the 2N consecutive vibration elements.

At a tenth object of invention, the present invention resides in an ultrasound diagnostic apparatus which is characterized by comprising: a transmitter or receiver having a 0th through (N−1)th channels; a high voltage switch including a 0th through (M−1)th switches, where M has a value of N multiplied by a natural number k of 2 or larger; and a sector probe having vibration elements of L in number, where N<L≦M, which are aligned in the order from the 0th through (L−1)th vibration elements, each n-th channel, where n takes 0 through N−1, being connected in parallel fashion to the n-th switch, the (n+N)th switch, . . . , and the (n+(k−1)N)th switch, the 0th through (L−1)th vibration elements of the sector probe being connected to the 0th through (L−1)th switches, respectively. The ultrasound diagnostic apparatus further comprises a switch control means which turns on the (L/2−N/2)th through (L/2+N/2−1)th switches, and turns off other switches which are connected with vibration elements.

The ultrasound diagnostic apparatus of the tenth object of invention is capable of implementing the sector probe driving method of the second object of invention properly.

At an eleventh object of invention, the present invention resides in an ultrasound diagnostic apparatus which is characterized by comprising: a transmitter or receiver having a 0th through (N−1)th channels; a high voltage switch including a 0th through (M−1)th switches, where M has a value of N multiplied by a natural number k of 2 or larger; and a sector probe having vibration elements of L in number, where N<L≦M, which are aligned in the order from the 0th through (L−1)th vibration elements, each n-th channel, where n takes 0 through N−1, being connected in parallel fashion to the n-th switch, the (n+N)th switch, . . . , and the (n+(k−1)N)th switch, the 0th through (L−1)th vibration elements of the sector probe being connected to the 0th through (L−1)th switches, respectively. The ultrasound diagnostic apparatus further comprises a switch control means which selects, out of the 0th through (L−1)th switches, vibration elements of N in number which are located at a constant pitch or virtually constant pitch and are not connected to same channels and turns on the N switches only, and turns off other switches which are connected with vibration elements.

The ultrasound diagnostic apparatus of the eleventh object of invention is capable of implementing the sector probe driving method of the first viewpoint properly.

At a twelfth object of invention, the present invention resides in an ultrasound diagnostic apparatus which is characterized by comprising: a transmitter or receiver having a 0th through (N−1)th channels; a high voltage switch including a 0th through (M−1)th switches, where M has a value of N multiplied by a natural number k of 2 or larger; and a sector probe having vibration elements of L in number, where N<L≦M, which are aligned in the order from the 0th through (L−1)th vibration elements, each n-th channel, where n takes 0 through N−1, being connected in parallel fashion to the n-th switch, the (n+N)th switch, . . . , and the (n+(k−1)N)th switch, the 0th through (L−1)th vibration elements of the sector probe being connected to the 0th through (L−1)th switches, respectively. The ultrasound diagnostic apparatus further comprises a switch control means which selects, out of the 0th through (L−1)th switches, vibration elements of N in number which are located at random and are not connected to same channels and turns on the N switches only, and turns off other switches which are connected with vibration elements.

The ultrasound diagnostic apparatus of the twelfth object of invention is capable of implementing the sector probe driving method of the third object of invention properly.

At a thirteenth object of invention, the present invention resides in an ultrasound diagnostic apparatus which is characterized by comprising: a transmitter or receiver having a 0th through (N−1)th channels; a high voltage switch including a 0th through (M−1)th switches, where M has a value of N multiplied by a natural number k of 2 or larger; and a sector probe having vibration elements of L in number, where N<L≦M, which are aligned in the order from the 0th through (L−1)th vibration elements, each n-th channel, where n takes 0 through N−1, being connected in parallel fashion to the n-th switch, the (n+N)th switch, . . . , and the (n+(k−1)N)th switch, the 0th through (L−1)th vibration elements of the sector probe being connected to the 0th through (L−1)th switches, respectively. The ultrasound diagnostic apparatus further comprises a switch control means which selects, out of the 0th through (L/2−1)th switches, vibration elements of N/2 in number which are located at random and are not connected to same channels and turns on the associated N/2 switches only, and selects, out of the (L/2)th through (L−1)th switches, switches of N/2 in number which correspond to vibration elements located symmetrically or nearly symmetrically to the vibration elements which correspond to the turned-on switches among the 0th through (L/2−1)th switches across the middle of the alignment of vibration elements and are not connected to same channels and to the channels used by the turned-on switches among the 0th through (L/2−1)th switches and turns on these N/2 switches only.

The ultrasound diagnostic apparatus of the thirteenth object of invention is capable of implementing the sector probe driving method of the fourth object of invention properly.

At a fourteenth object of invention, the present invention resides in an ultrasound diagnostic apparatus which is derived from the above-mentioned arrangement, the apparatus being characterized in that the switch control means selects switches which correspond to vibration elements located at the middle or nearly middle of the alignment of vibration elements at higher probabilities than probabilities of selection of switches which correspond to vibration elements located far from the middle of the alignment of vibration elements.

The ultrasound diagnostic apparatus of the fourteenth object of invention is capable of implementing the sector probe driving method of the fifth object of invention properly.

At a fifteenth object of invention, the present invention resides in an ultrasound diagnostic apparatus which is derived from the above-mentioned arrangement, the apparatus being characterized in that the switch control means selects, out of switches corresponding to vibration elements which are located far from the middle of the alignment of vibration elements, one set of odd-numbered switches or even-numbered switches at higher probabilities than probabilities of selection of another set of switches.

The ultrasound diagnostic apparatus of the fifteenth object of invention is capable of implementing the sector probe driving method of the sixth object of invention properly.

At a sixteenth object of invention, the present invention resides in an ultrasound diagnostic apparatus which is characterized by comprising: a transmitter or receiver having a 0th through (N−1)th channels; a high voltage switch including a 0th through (M−1)th switches, where M has a value of N multiplied by a natural number k of 2 or larger; and a sector probe having vibration elements of L in number, where N<L≦M, which are aligned in the order from the 0th through (L−1)th vibration elements, each n-th channel, where n takes 0 through N−1, being connected in parallel fashion to the n-th switch, the (n+N)th switch, . . . , and the (n+(k−1)N)th switch, the 0th through (L−1)th vibration elements of the sector probe being connected to the 0th through (L−1)th switches, respectively. The ultrasound diagnostic apparatus further comprises a switch control means which turns on a (L/2−C/2)th through (L/2+C/2−1)th switches, turns on every b-th switch among the (L/2−C/2−(b+1)(N−C)/2)th through (L/2−C/2−1)th switches, turns on every b-th switch among the (L/2−C/2+b)th through (L/2+C/2−1+(b+1)(N−C)/2)th switches, and turns off other switches which are connected with vibration elements.

The ultrasound diagnostic apparatus of the sixteenth object of invention is capable of implementing the sector probe driving method of the seventh object of invention properly.

At a seventeenth object of invention, the present invention resides in an ultrasound diagnostic apparatus which is characterized by comprising: a transmitter or receiver having a 0th through (N−1)th channels; a high voltage switch including a 0th through (M−1)th switches, where M has a value of N multiplied by a natural number k of 2 or larger; and a sector probe having vibration elements of L in number, where N<L≦M, which are aligned in the order from the 0th through (L−1)th vibration elements, each n-th channel, where n takes 0 through N−1, being connected in parallel fashion to the n-th switch, the (n+N)th switch, . . . , and the (n+(k−1)N)th switch, the 0th through (L−1)th vibration elements of the sector probe being connected to the 0th through (L−1)th switches, respectively. The ultrasound diagnostic apparatus further comprises: at least two of the switch control means of the above-mentioned arrangement; and a switch control mode selection means which selects one of the two switch control means depending on at least one of the ultrasound diagnostic mode, scanning depth, scanning angle, and ultrasound frequency.

The ultrasound diagnostic apparatus of the seventeenth object of invention is capable of implementing the sector probe driving method of the eighth object of invention properly.

According to the inventive sector probe driving method and ultrasound diagnostic apparatus, it is possible to implement the sector scanning properly by driving the sector probe by use of the transmitter/receiver for the convex probe and linear probe.

Further objects and advantages of the present invention will be apparent from the following description of the preferred embodiments of the invention as illustrated in the accompanying drawings.

DETAILED DESCRIPTION OF THE INVENTION

The present invention will be explained in more detail in regard to illustrated embodiments. The present invention is not confined to these embodiments however.

First Embodiment

Figure 1:
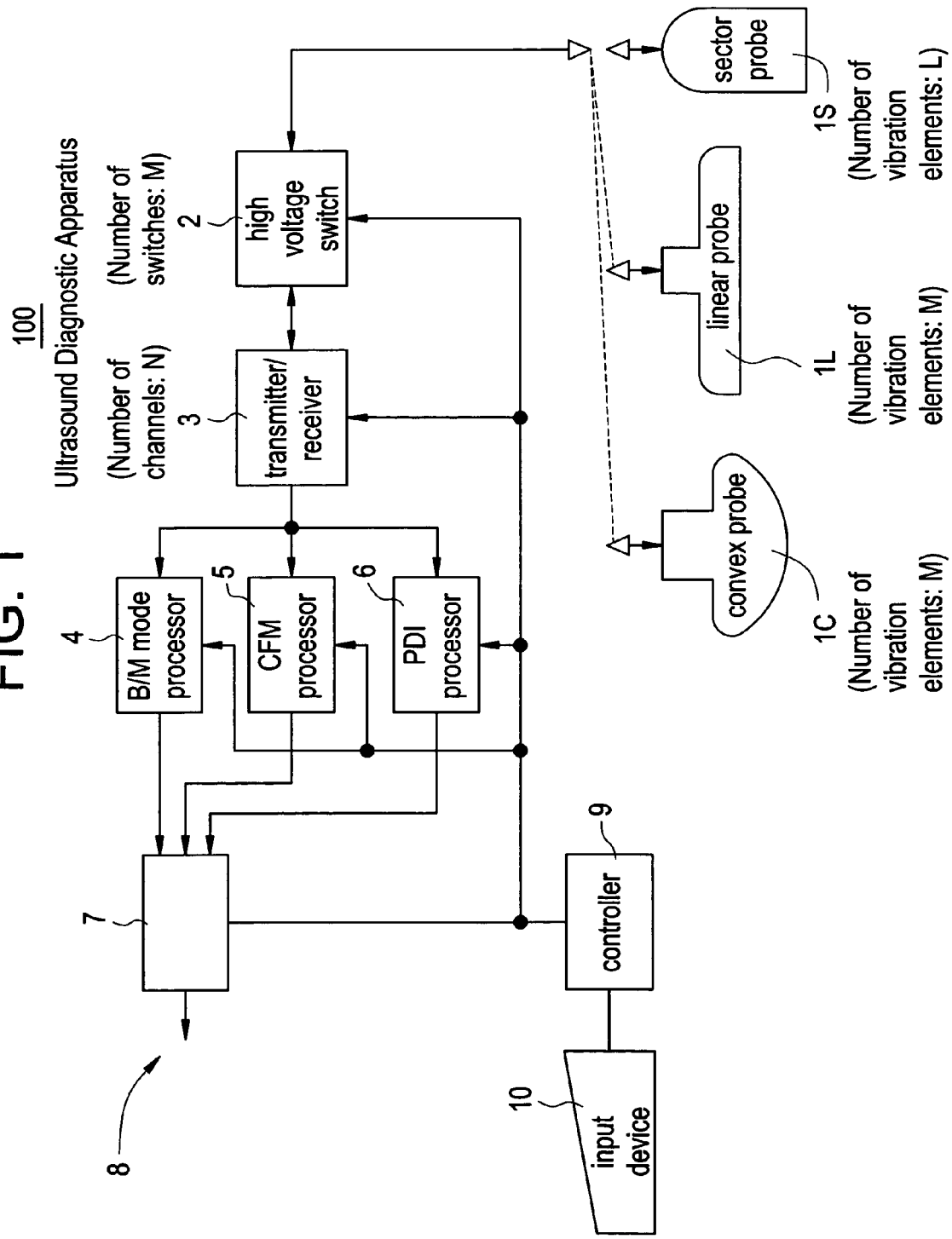
FIG. 1 is a block diagram showing the arrangement of the ultrasound diagnostic apparatus of the first embodiment.

FIG. 1 is a block diagram showing an ultrasound diagnostic apparatus 100 based on a first embodiment.

The ultrasound diagnostic apparatus 100 includes a convex probe 1C having vibration elements of M in number, a linear probe 1L having vibration elements of M in number, a sector probe 1S having vibration elements of L in number, a high voltage switch 2 including switches of M in number, a transmitter/receiver 3 of N channels, a B/M mode processor 4, a CFM (Color Flow Mapping) processor 5, a PDI (Power Doppler Image) processor 6, a DSC (Digital Scan Converter) 7, a display device 8, a controller 9, and an input device 10.

Figure 2:
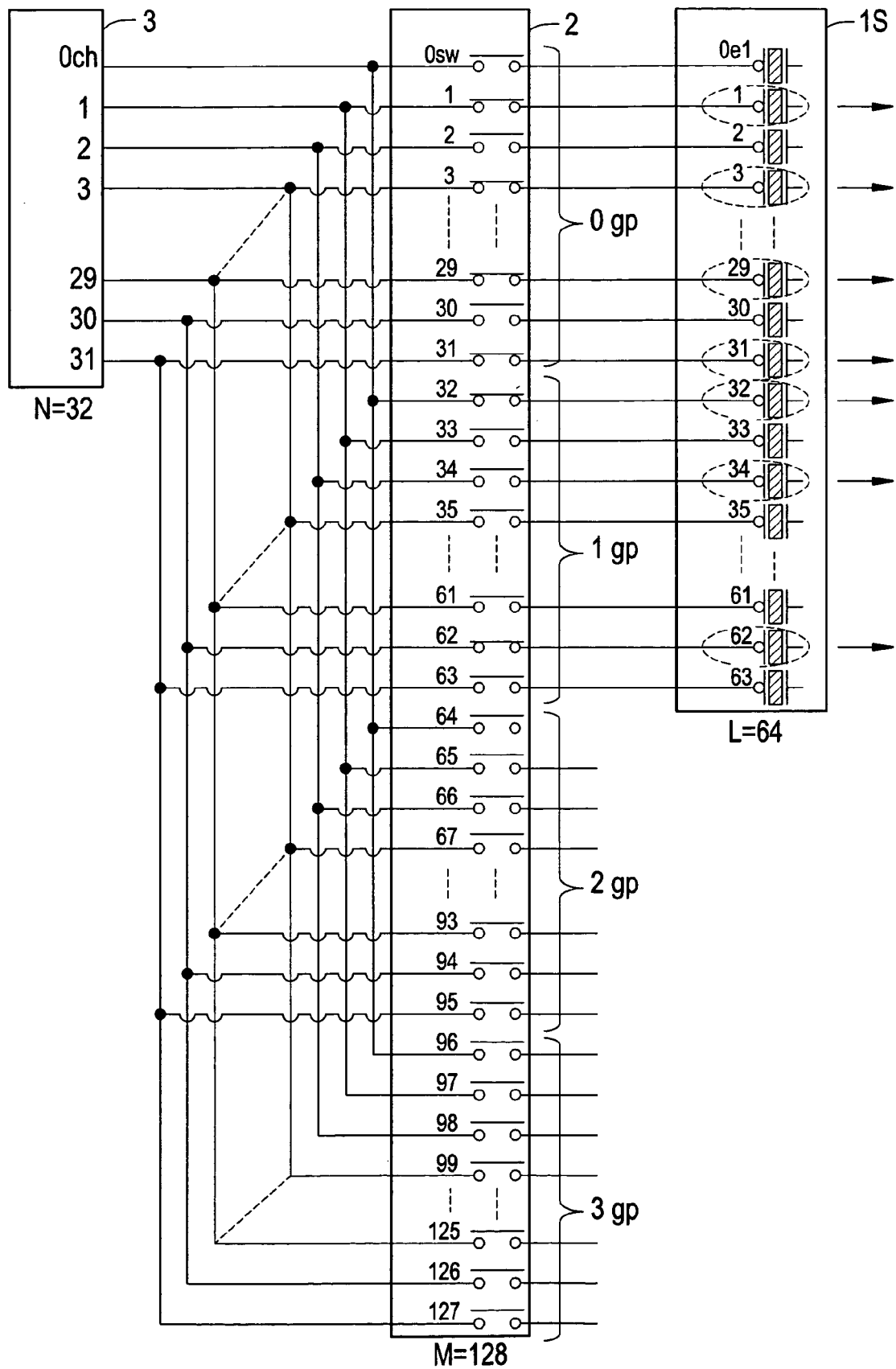
FIG. 2 is an explanatory diagram showing the connection among the sector probe, high voltage switch, and transmitter/receiver based on the first embodiment.

FIG. 2 is an explanatory diagram showing the connection among the sector probe 1S, high voltage switch 2, and transmitter/receiver 3 of the first embodiment. The parameters are set to be N=32, M=128 and L=64 in this embodiment.

Each n-th channel, where n takes 0 through 31, is connected in parallel fashion to the n-th switch, the (n+32)th switch, . . . , and the (n+96)th switch.

The sector probe 1S has its 0th through 63rd vibration elements connected to the 0th through 63rd switches, respectively.

The controller 9 unites each set of a m-th through (m+31)th switches, where m takes 0, 32, 64 and 96, into a (m/32)th switch group, selects two switch groups in which all switches are connected with vibration elements, turns on only odd-numbered switches for one switch group, turns on only even-numbered switches for another switch group, and turns off switches which are of other switch groups and connected with vibration elements. Specifically, the controller 9 selects the 0th switch group and 1st switch group, turns on only the odd-numbered switches for the 0th switch group, and turns on only the even-numbered switches for the 1 st switch group. Consequently, only the vibration elements of odd numbers 1, 3, . . . , 31 among the vibration elements corresponding to the 0th switch group are driven, and only the vibration elements of even numbers 32, 34, . . . , 62 among the vibration elements corresponding to the 1 st switch group are driven.

Figure 3:
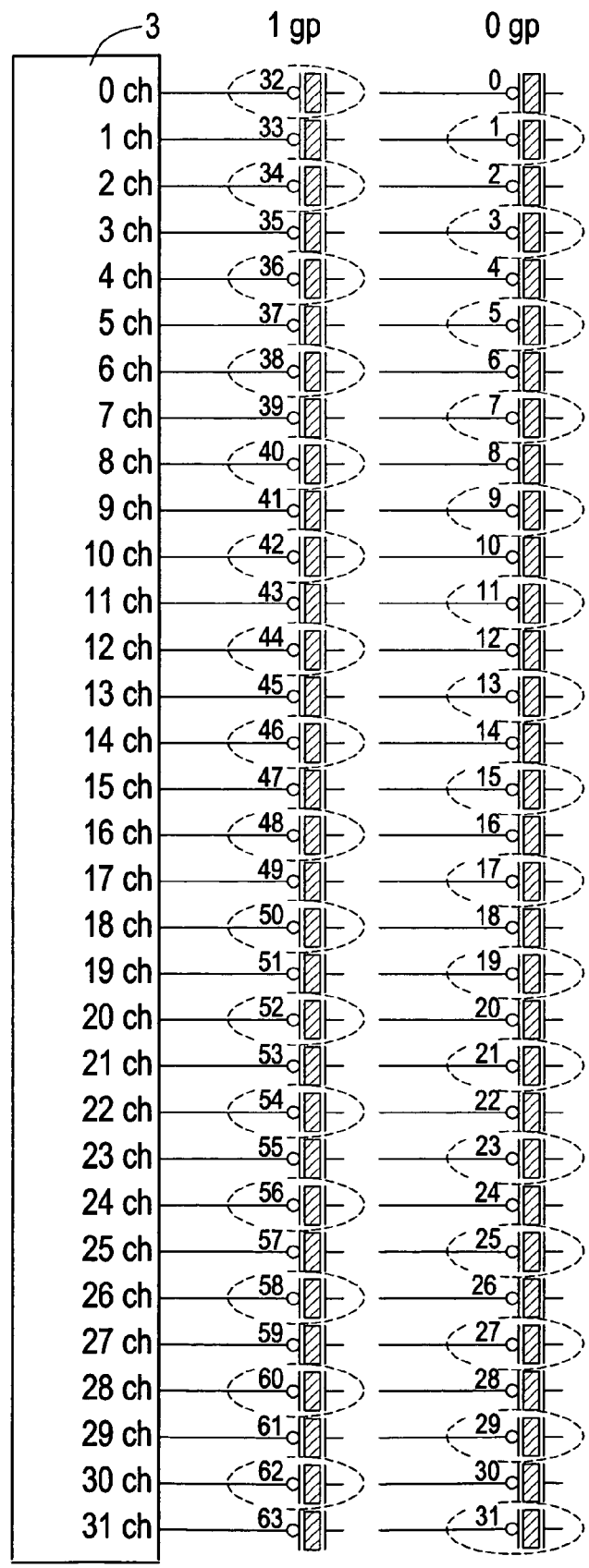
FIG. 3 is an explanatory diagram showing the correspondence between the channels of the transmitter/receiver and the vibration elements of the sector probe based on the first embodiment.

FIG. 3 is an explanatory diagram showing the correspondence between the channels of the transmitter/receiver 3 and the vibration elements of the sector probe 1S of the first embodiment. Vibration elements to be driven are marked by dashed ellipsoids.

Only the vibration elements of odd numbers 1, 3, . . . , 31 among the vibration elements corresponding to the 0th switch group are driven, and only the vibration elements of even numbers 32, 34, . . . , 62 among the vibration elements corresponding to the 1 st switch group are driven.

FIG. 3 reveals that 32 vibration elements located at a virtually constant pitch are driven selectively, and it becomes possible for the transmitter/receiver 3 to implement the sector scanning by using the sector probe 1S. In addition, the apparatus can have a large aperture.

Figure 4:
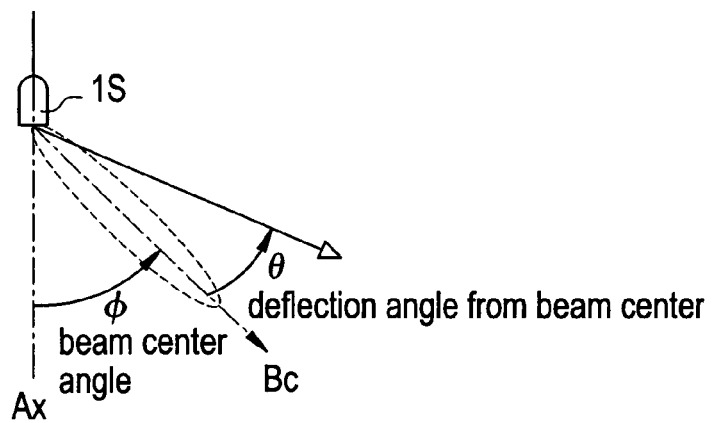
FIG. 4 is an explanatory diagram of the beam center angle φ and deflection angle θ.

FIG. 4 is an explanatory diagram of the beam center angle $\phi$ and the deflection angle $\theta$ from the beam center.

The beam center angle $\phi$ is the angle of beam center measured from the central axis Ax of the sector probe 1S.

The deflection angle $\theta$ from the beam center is the angle of sound beam measured from the beam center Bc.

Figure 5:
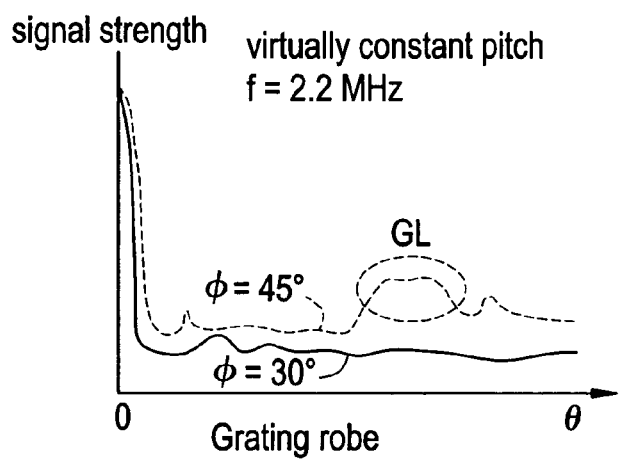
FIG. 5 is a characteristic graph of the signal strength with respect to the deflection angle θ when the beam center angle φ is 30° and the signal strength with respect to the deflection angle θ when the beam center angle φ is 45°.

FIG. 5 is a characteristic graph of the signal strength with respect to the deflection angle $\theta$ when the beam center angle $\phi$ is 30° and the signal strength with respect to the deflection angle $\theta$ when the beam center angle $\theta$ is 45°. The frequency f is 2.2 MHz.

FIG. 5 reveals that no grating robe emerges when the beam center angle $\phi$ is 30°, while a grating lobe GL emerges when the beam center angle $\phi$ is 45°. The graph reveals that the range of scanning angle is preferably set to be: beam center angle $|\phi| \leq 37.5°$ (middle of 300 and 45°) in order to prevent the emergence of grating lobe.

Figure 6:
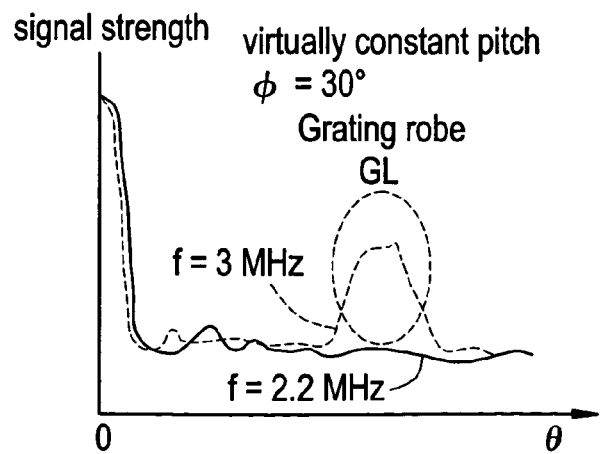
FIG. 6 is a characteristic graph of the signal strength with respect to the deflection angle θ when the frequency f is 2.2 MHz and the signal strength with respect to the deflection angle θ when the frequency f is 3 MHz.

FIG. 6 is a characteristic graph of the signal strength with respect to the deflection angle $\theta$ when the frequency f is 2.2 MHz and the signal strength with respect to the deflection angle $\theta$ when the frequency is 3 MHz. The beam center angle $\phi$ is 30°.

FIG. 6 reveals that no grating lobe emerges when the frequency is 2.2 MHz, while a grating lobe GL emerges when the frequency is 3 MHz. The graph reveals that the frequency is preferably set below 2.6 MHz (middle of 2.2 MHz and 3 MHz) in order to prevent the emergence of grating lobe.

In harmonic imaging, in which a low transmission frequency is used and harmonic components scarcely arise at the sound pressure of grating lobe, the range of scanning angle can be set to be: beam center angle $|\phi| \leq 45°$.

Second Embodiment

Figure 7:
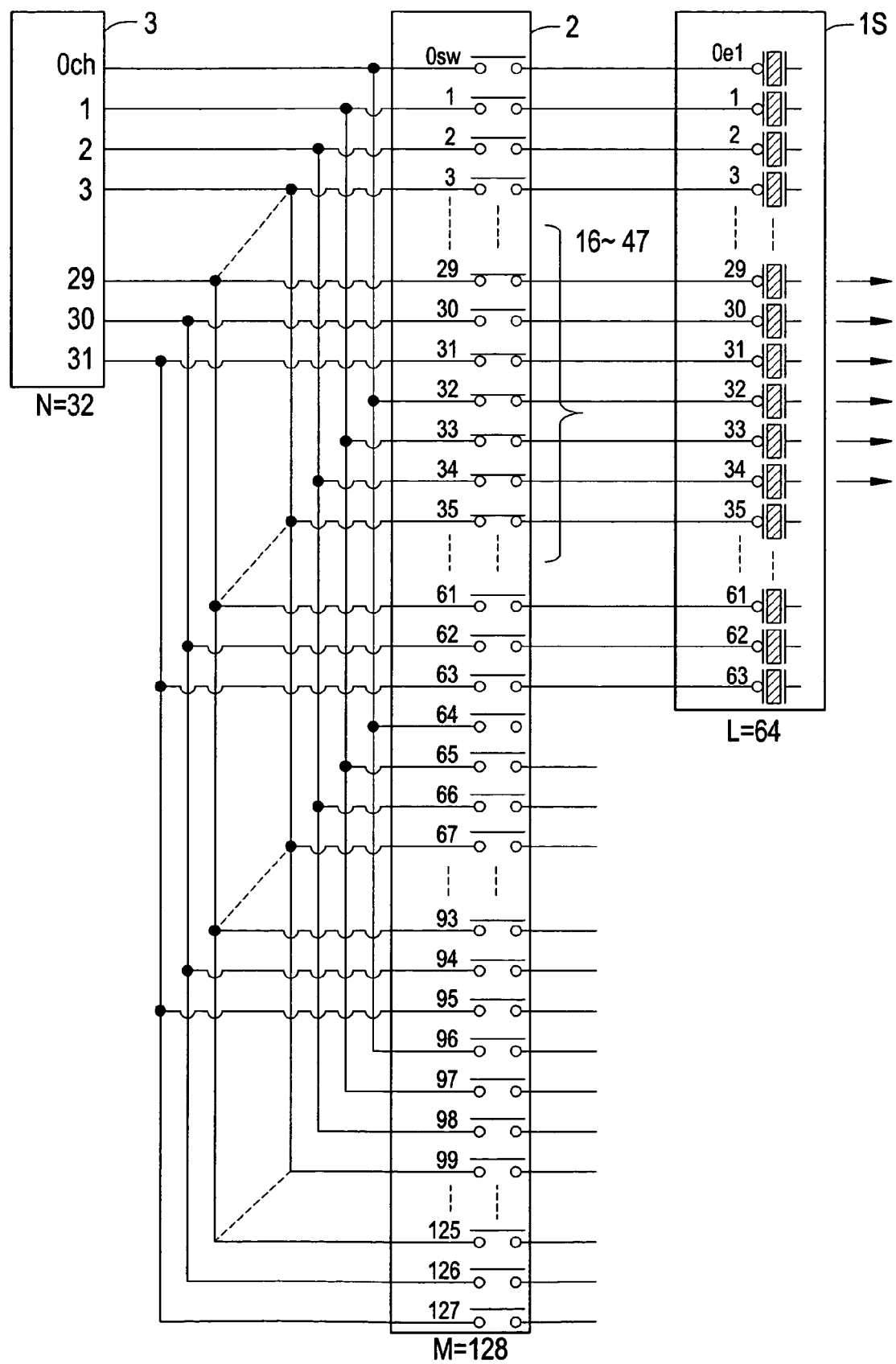
FIG. 7 is an explanatory diagram showing the connection among the sector probe, high voltage switch, and transmitter/receiver based on the second embodiment.

FIG. 7 is an explanatory diagram showing the connection among the sector probe 1S, high voltage switch 2, and transmitter/receiver 3 of a second embodiment. The parameters are set to be N=32, M=128 and L=64 in this embodiment.

Each n-th channel, where n takes 0 through 31, is connected in parallel fashion to the n-th switch, the (n+32)th switch, . . . , and the (n+96)th switch.

The sector probe 1S has its 0th through 63rd vibration elements connected to the 0th through 63rd switches, respectively.

The controller 9 turns on the 16th through 47th switches and turns off other switches which are connected with vibration elements. Consequently, only the 16th through 47th vibration elements located in the central section of the alignment of vibration elements are driven.

Figure 8:
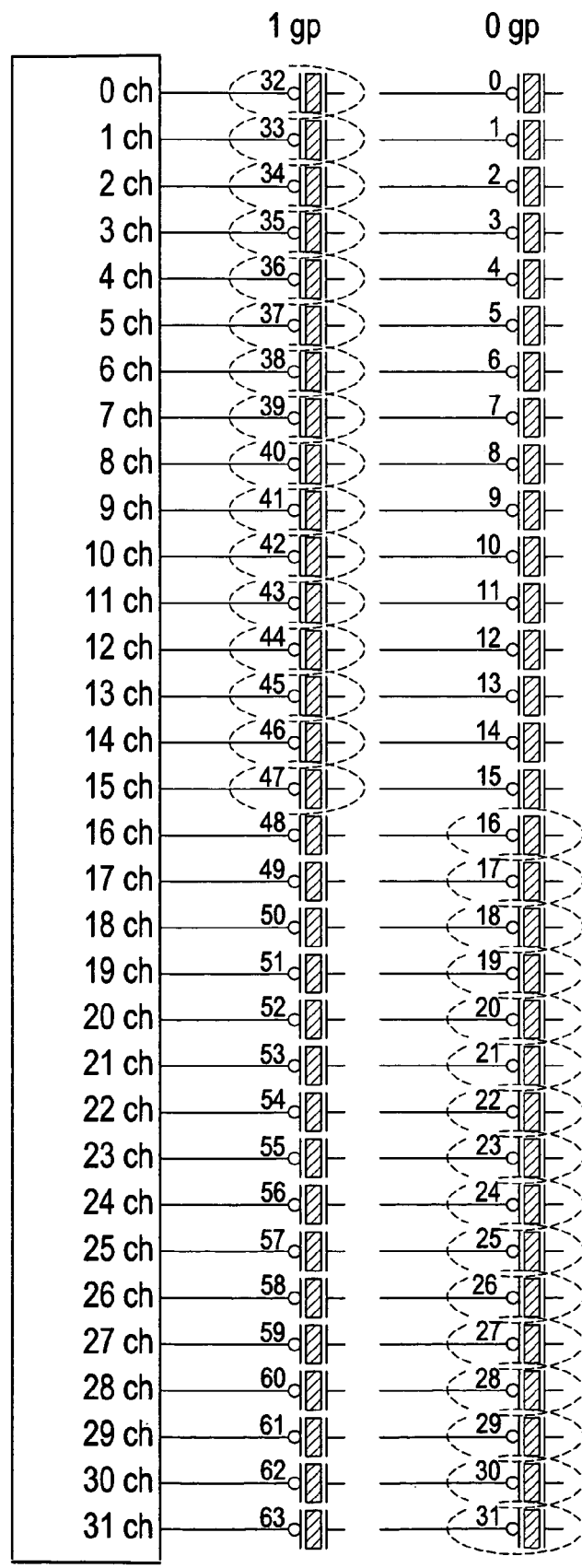
FIG. 8 is an explanatory diagram showing the correspondence between the channels of the transmitter/receiver and the vibration elements of the sector probe based on the second embodiment.

FIG. 8 is an explanatory diagram showing the correspondence between the channels of the transmitter/receiver 3 and the vibration elements of the sector probe 1S of the second embodiment. Vibration elements to be driven are marked by dashed ellipsoids.

Only the 16th through 47th vibration elements located in the central section of the alignment of vibration elements are driven.

FIG. 8 reveals that selective driving of 32 contiguous vibration elements enables the sector scanning by use of the sector probe 1S. In the B/M mode which uses the fundamental wave, an image of less grating lobe can be obtained. Due to a small aperture, a deep portion has a low resolution. Therefore, this apparatus is preferably used for the observation of a shallow portion (e.g., in a depth of 12 cm or smaller) or for the CFM or PDI which do not require a high resolution.

Third Embodiment

Figure 9:
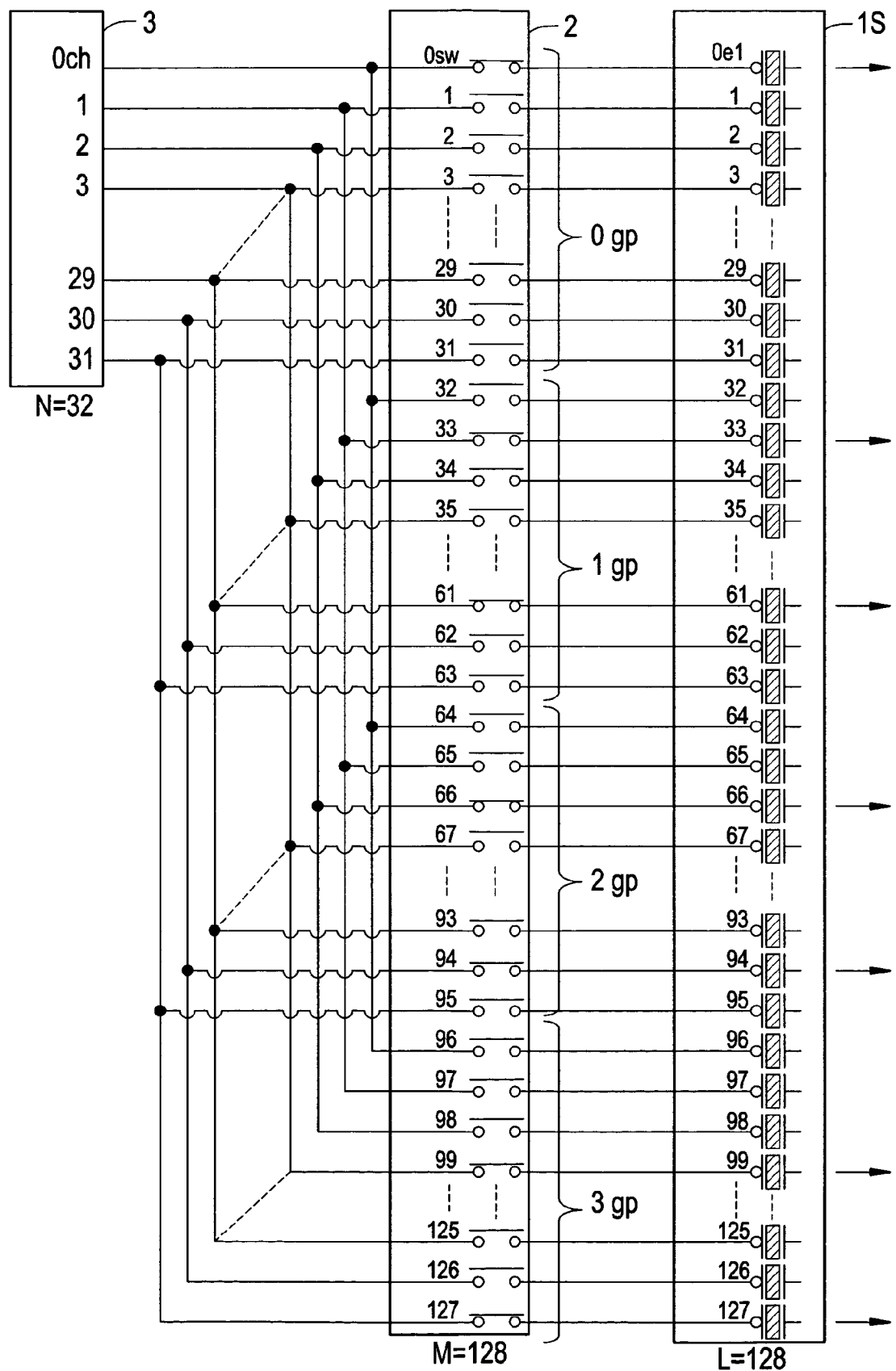
FIG. 9 is an explanatory diagram showing the connection among the sector probe, high voltage switch, and transmitter/receiver based on the third embodiment.

FIG. 9 is an explanatory diagram showing the connection among the sector probe 1S, high voltage switch 2, and transmitter/receiver 3 of a third embodiment. The parameters are set to be N=32, M=128 and L=128 in this embodiment.

Each n-th channel, where n takes 0 through 31, is connected in parallel fashion to the n-th switch, the (n+32)th switch, . . . , and the (n+96)th switch.

The sector probe 1S has its 0th through 127th vibration elements connected to the 0th through 127th switches, respectively.

Each set of a m-th through (m+31)th switches, where m takes 0, 32, 64 and 96), are united to be a (m/32)th switch group.

The controller 9 selects 32 vibration elements which are located at a constant pitch or virtually constant pitch and are not connected to same channels, turns on the 32 switches only, and turns off other switches which are connected with vibration elements. Consequently, only 32 vibration elements which are distributed at a constant pitch or virtually constant pitch in the alignment of vibration elements are driven.

Figure 10:
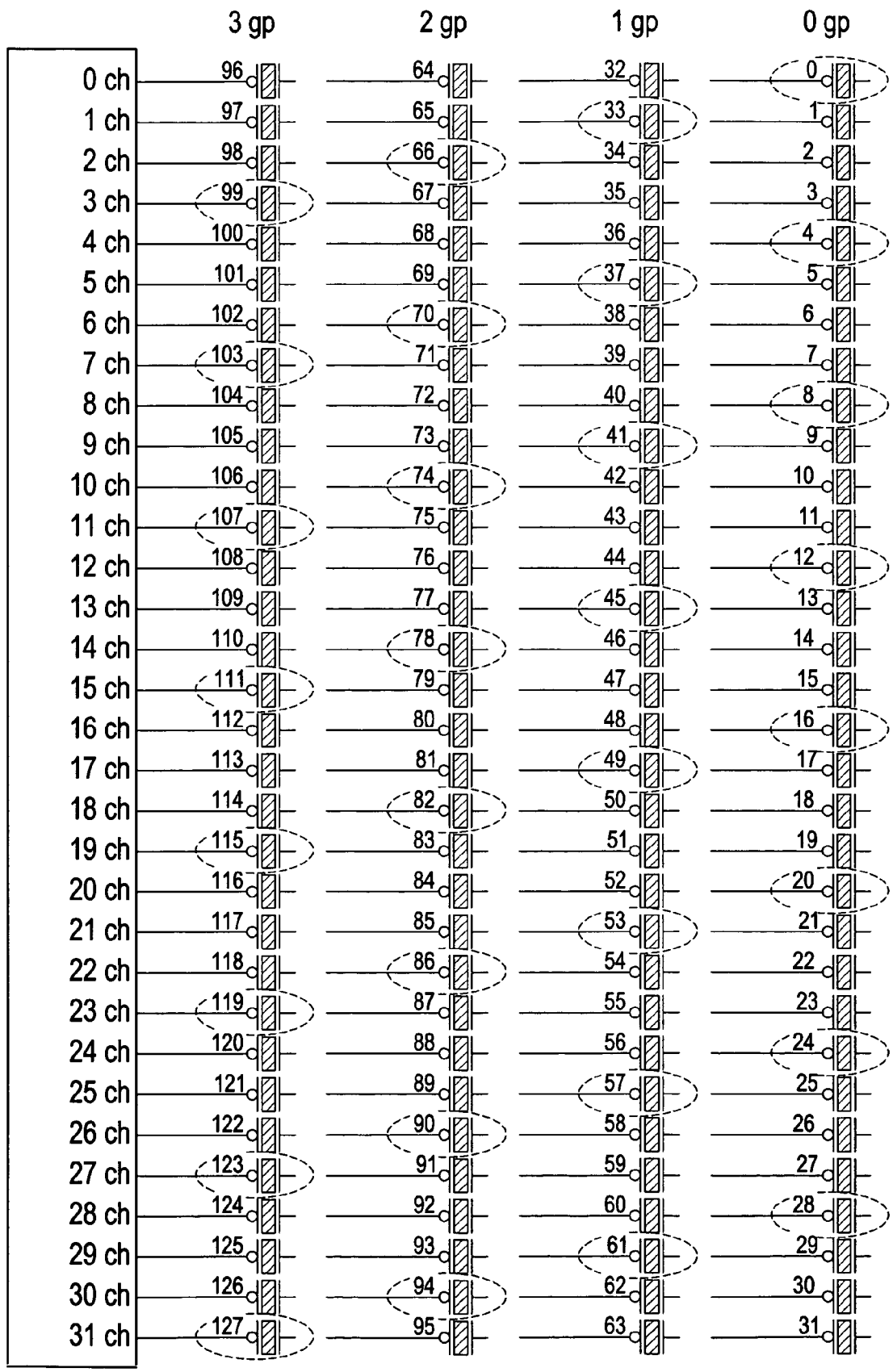
FIG. 10 is an explanatory diagram showing the correspondence between the channels of the transmitter/receiver and the vibration elements of the sector probe based on the third embodiment.

FIG. 10 is an explanatory diagram showing the correspondence between the channels of the transmitter/receiver 3 and the vibration elements of the sector probe 1S of the third embodiment. Vibration elements to be driven are marked by dashed ellipsoids.

FIG. 10 reveals that for each n-th channel, where n takes 0 through 31, only a switch which belongs to a mod $\{n/4\}$th switch group is turned on to drive a corresponding vibration element, where mod $\{\alpha/\beta\}$ is a function which gives the modulus of $\alpha/\beta$.

More generally, for each n-th channel, where n takes 0 through N, only a switch which belongs to a mod $\{n/k\}$th switch group, where k=M/N, is turned on.

The third embodiment has the similar operational characteristics as the first embodiment.

Fourth Embodiment

Figure 11:
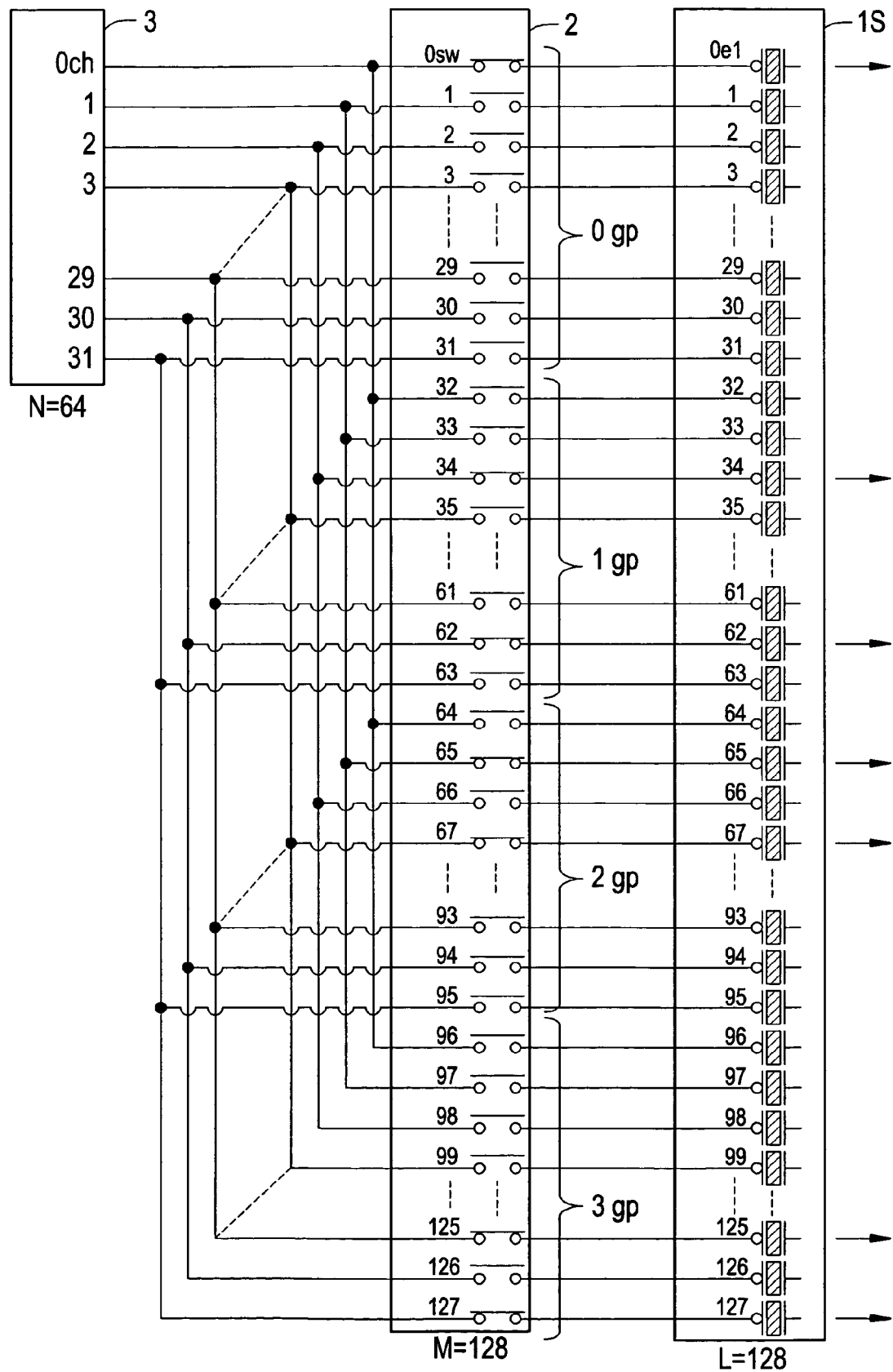
FIG. 11 is an explanatory diagram showing the connection among the sector probe, high voltage switch, and transmitter/receiver based on the fourth embodiment.

FIG. 11 is an explanatory diagram showing the connection among the sector probe 1S, high voltage switch 2, and transmitter/receiver 3 of a fourth embodiment. The parameters are set to be N=32, M=128 and L=128 in this embodiment.

Each n-th channel, where n takes 0 through 31, is connected in parallel fashion to the n-th switch, the (n+32)th switch, . . . , and the (n+96)th switch.

The sector probe 1S has its 0th through 127th vibration elements connected to the 0th through 127th switches, respectively.

Each set of a m-th through (m+31)th switches, where m takes 0, 32, 64 and 96) are united to be a (m/32)th switch group.

The controller 9 selects, out of the 0th through 127th switches, 32 vibration elements which are located at random and are not connected to same channels, turns on the 32 switches only, and turns off other switches which are connected with vibration elements. Consequently, only 32 vibration elements which are distributed at random in the alignment of vibration elements are driven.

Figure 12:
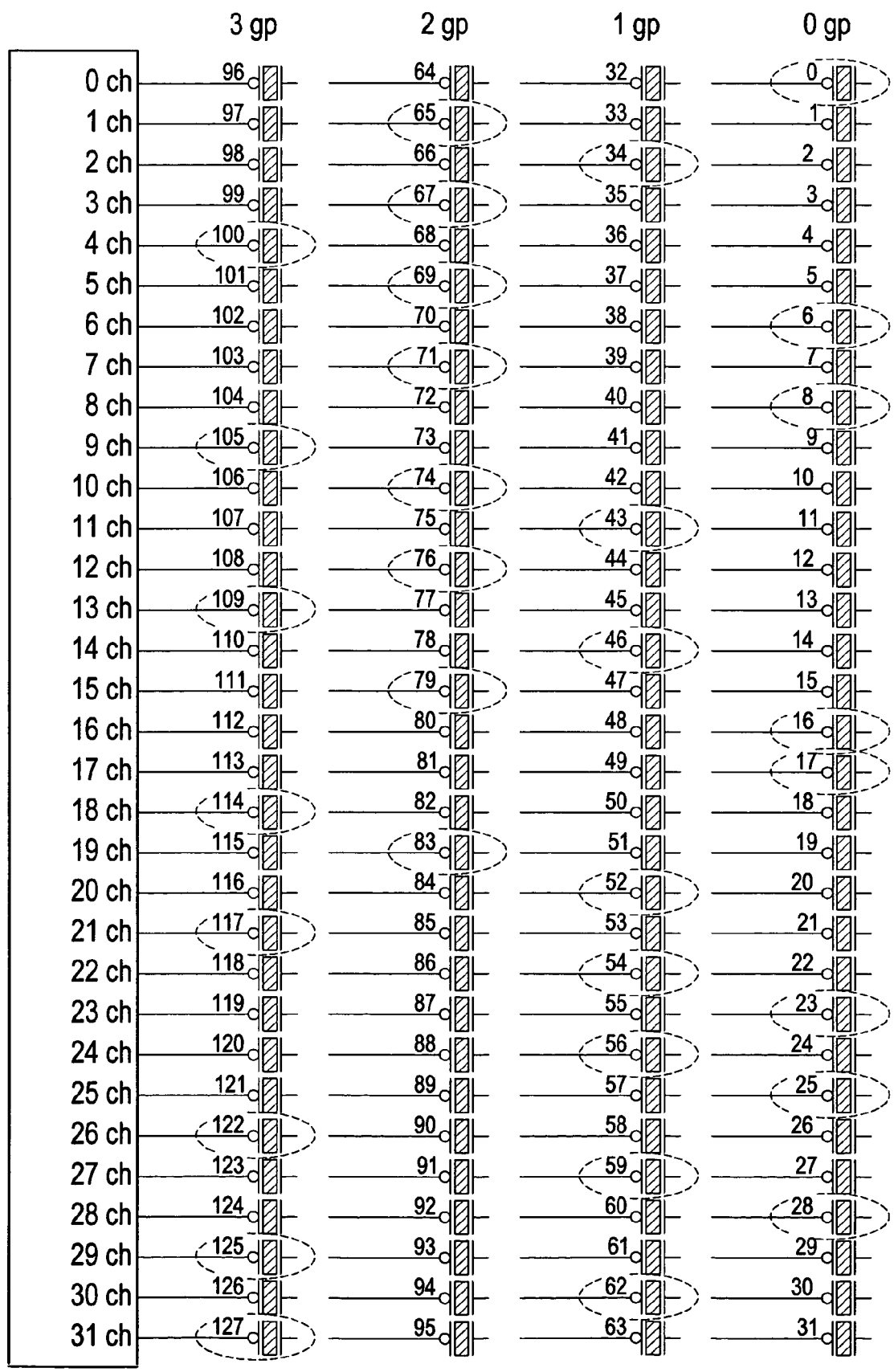
FIG. 12 is an explanatory diagram showing the correspondence between the channels of the transmitter/receiver and the vibration elements of the sector probe based on the fourth embodiment.

FIG. 12 is an explanatory diagram showing the correspondence between the channels of the transmitter/receiver 3 and the vibration elements of the sector probe 1S of the fourth embodiment. Vibration elements to be driven are marked by dashed ellipsoids.

FIG. 12 reveals that one of the four switch groups is selected at random for each channel, and only a switch which belongs to the selected switch group is turned on to drive the corresponding vibration element.

As shown in FIG. 12, selective driving of 32 vibration elements which are distributed at random in the alignment of vibration elements enables the sector scanning by use of the sector probe 1S. Based on the irregularity in pitch of the vibration elements to be driven, an image of less grating lobe can be obtained.

Fifth Embodiment

Figure 13:
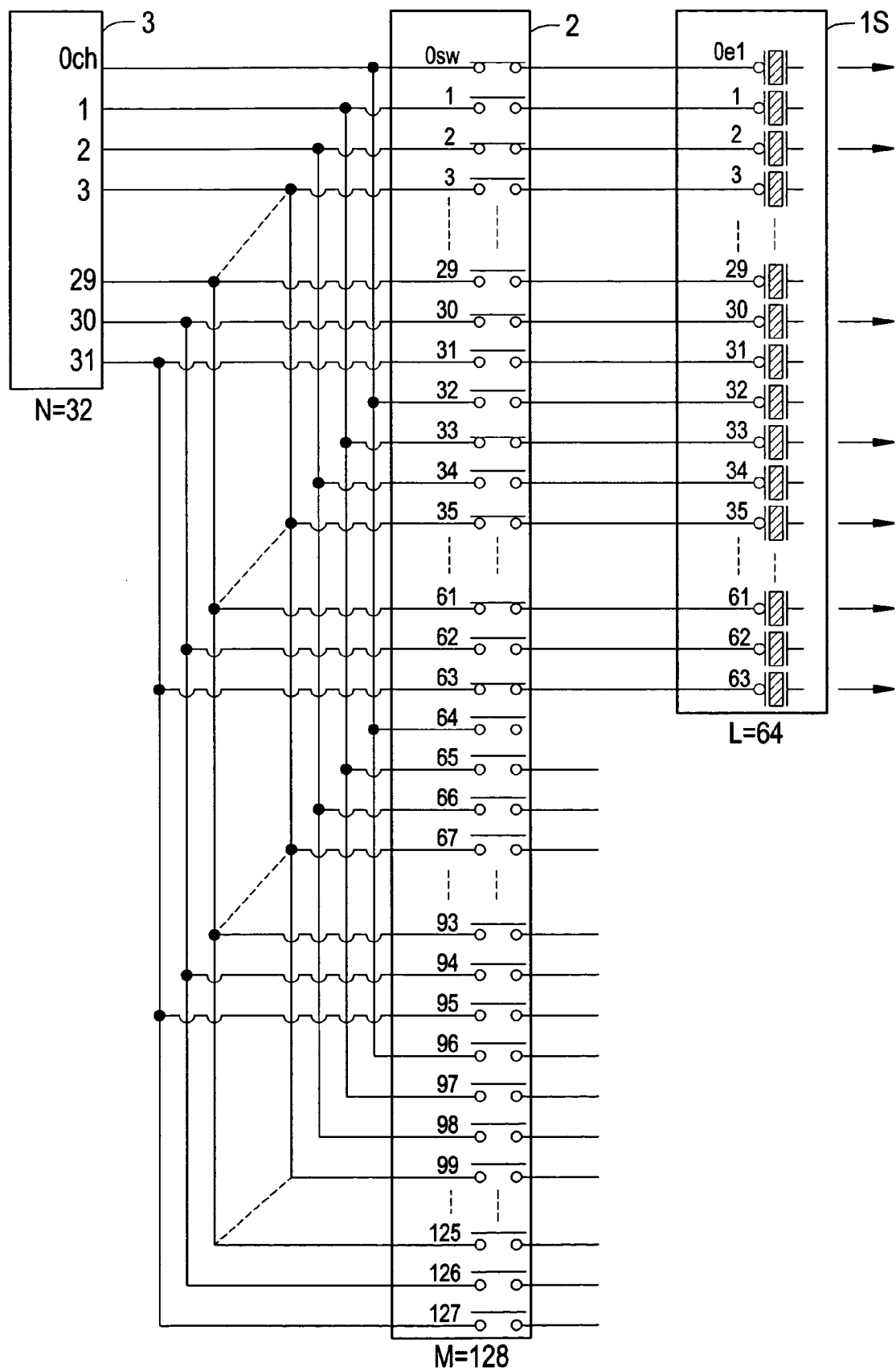
FIG. 13 is an explanatory diagram showing the connection among the sector probe, high voltage switch, and transmitter/receiver based on the fifth embodiment.

FIG. 13 is an explanatory diagram showing the connection among the sector probe 1S, high voltage switch 2, and transmitter/receiver 3 of a fifth embodiment. The parameters are set to be N=32, M=128 and L=64 in this embodiment.

Each n-th channel, where n takes 0 through 31, is connected in parallel fashion to the n-th switch, the (n+32)th switch, . . . , and the (n+96)th switch.

The sector probe 1S has its 0th through 63rd vibration elements connected to the 0th through 63rd switches, respectively.

Each set of a m-th through (m+31)th switches, where m takes 0, 32, 64 and 96), are united to be a (m/32)th switch group.

The controller 9 selects, out of the 0th through 31st switches, 16 vibration elements which are located at random and are not connected to same channels, and turns on the associated 16 switches only. Next, the controller 9 selects, out of the 32nd through 63rd switches, 16 switches which correspond to vibration elements located symmetrically or nearly symmetrically to the vibration elements which correspond to the turned-on switches among the 0th through 31st switches across the middle of the alignment of vibration elements and are not connected to same channels and to the channels used by the turned-on switches among the 0th through 31st switches, and turns on only these 16 switches. Consequently, only 32 vibration elements which are distributed at random in a half of the alignment of vibration elements and distributed virtually symmetrically in the middle of the alignment of vibration elements are driven.

Figure 14:
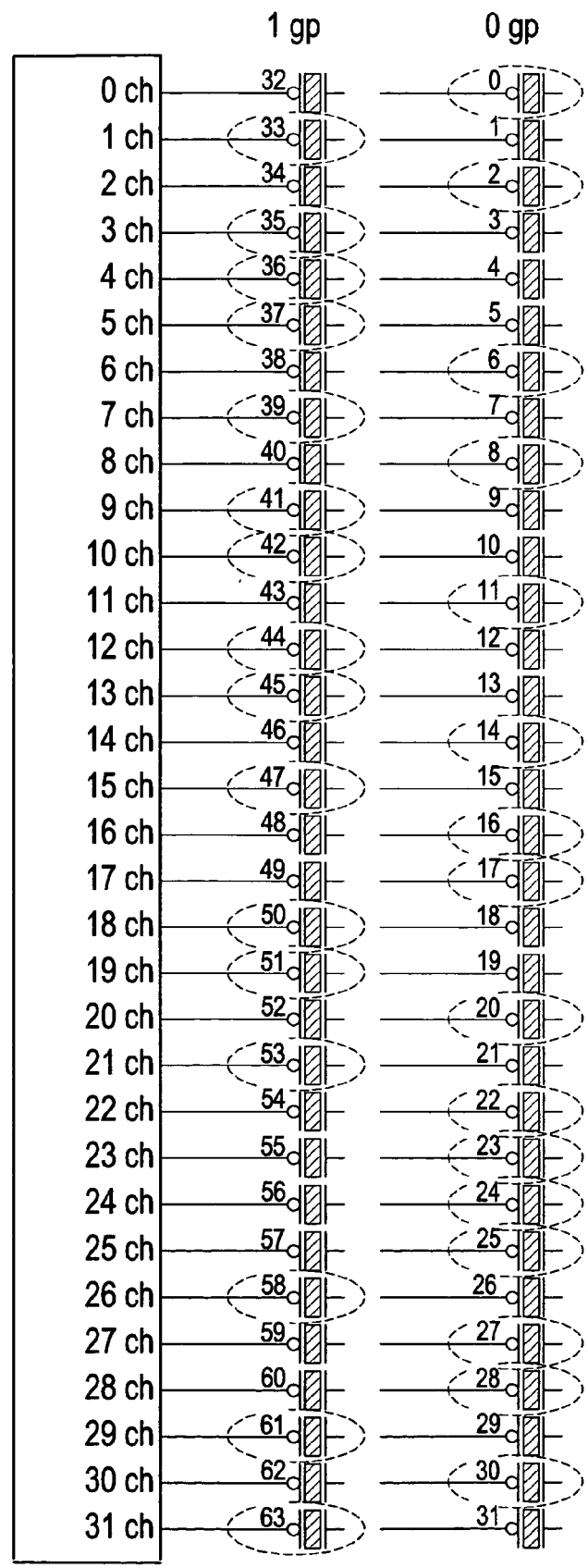
FIG. 14 is an explanatory diagram showing the correspondence between the channels of the transmitter/receiver and the vibration elements of the sector probe based on the fifth embodiment.

FIG. 14 is an explanatory diagram showing the correspondence between the channels of the transmitter/receiver 3 and the vibration elements of the sector probe 1S of the fifth embodiment. Vibration elements to be driven are marked by dashed ellipsoids.

FIG. 14 reveals that 16 vibration elements are selected at random out of the vibration elements of the 0th switch group, and only the switches corresponding to these vibration elements are turned on to drive the corresponding vibration elements. In addition, switches which correspond to the channels of the turned-off switches of the 0th switch group are selected out of the vibration elements of the 1st switch group, and only these switches are turned on to drive the corresponding vibration elements.

As shown in FIG. 14, selective driving of 32 vibration elements, which are distributed at random in a half of the alignment of vibration elements and distributed virtually symmetrically in the middle of the alignment of vibration elements, enables the sector scanning by use of the sector probe 1S.

Figure 15:
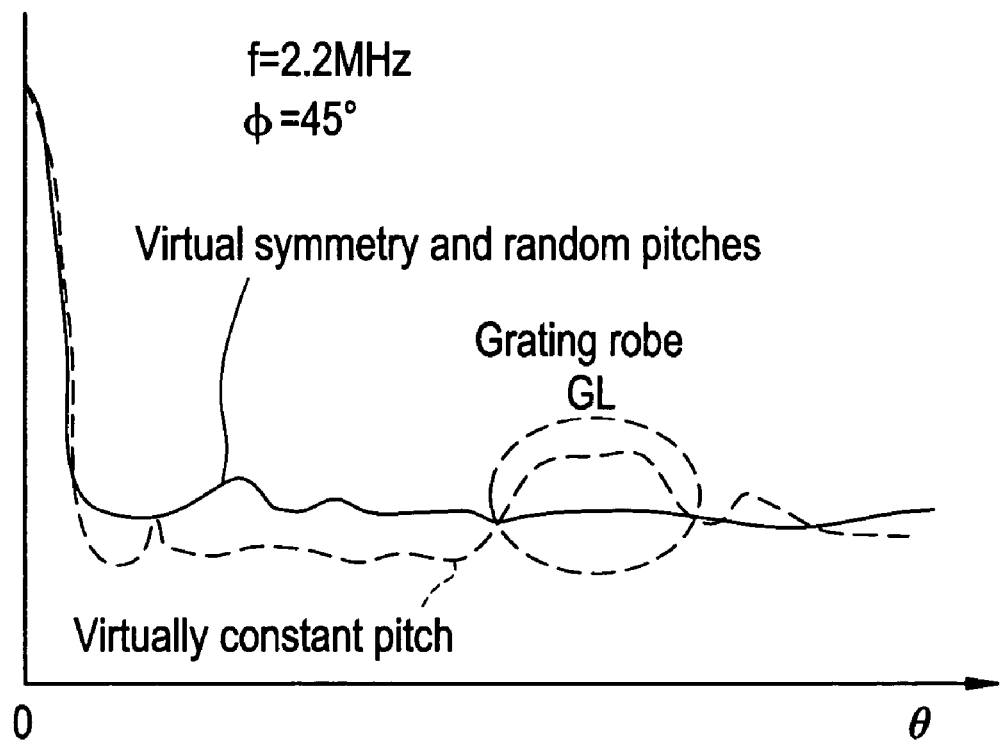
FIG. 15 is a characteristic graph of the signal strength with respect to the deflection angle θ when vibration elements which are distributed at a virtually constant pitch in the alignment of vibration elements are driven and the signal strength with respect to the deflection angle θ when vibration elements which are distributed at random in a half of the alignment of vibration elements and distributed virtually symmetrically in the middle of the alignment of vibration elements are driven.

FIG. 15 is a characteristic graph of the signal strength with respect to the deflection angle $\theta$ when vibration elements distributed at a virtually constant pitch in the alignment of vibration elements are driven (virtually constant pitch: first embodiment), and the signal strength with respect to the deflection angle $\theta$ when vibration elements, which are distributed at random in a half of the alignment of vibration elements and distributed virtually symmetrically in the middle of the alignment of vibration elements, are driven (virtual symmetry and random pitches: fifth embodiment). The frequency f is 2.2 MHz and the beam center angle $\phi$ is 45°.

FIG. 15 reveals that although the case of "virtual symmetry and random pitches" is inferior to the case of "virtually constant pitch" in the floor section of boom profile, it does not create a grating lobe. Accordingly, the vibration element selection at "virtual symmetry and random pitches" is found to be useful without problems for any imaging mode.

Sixth Embodiment

Figure 16:
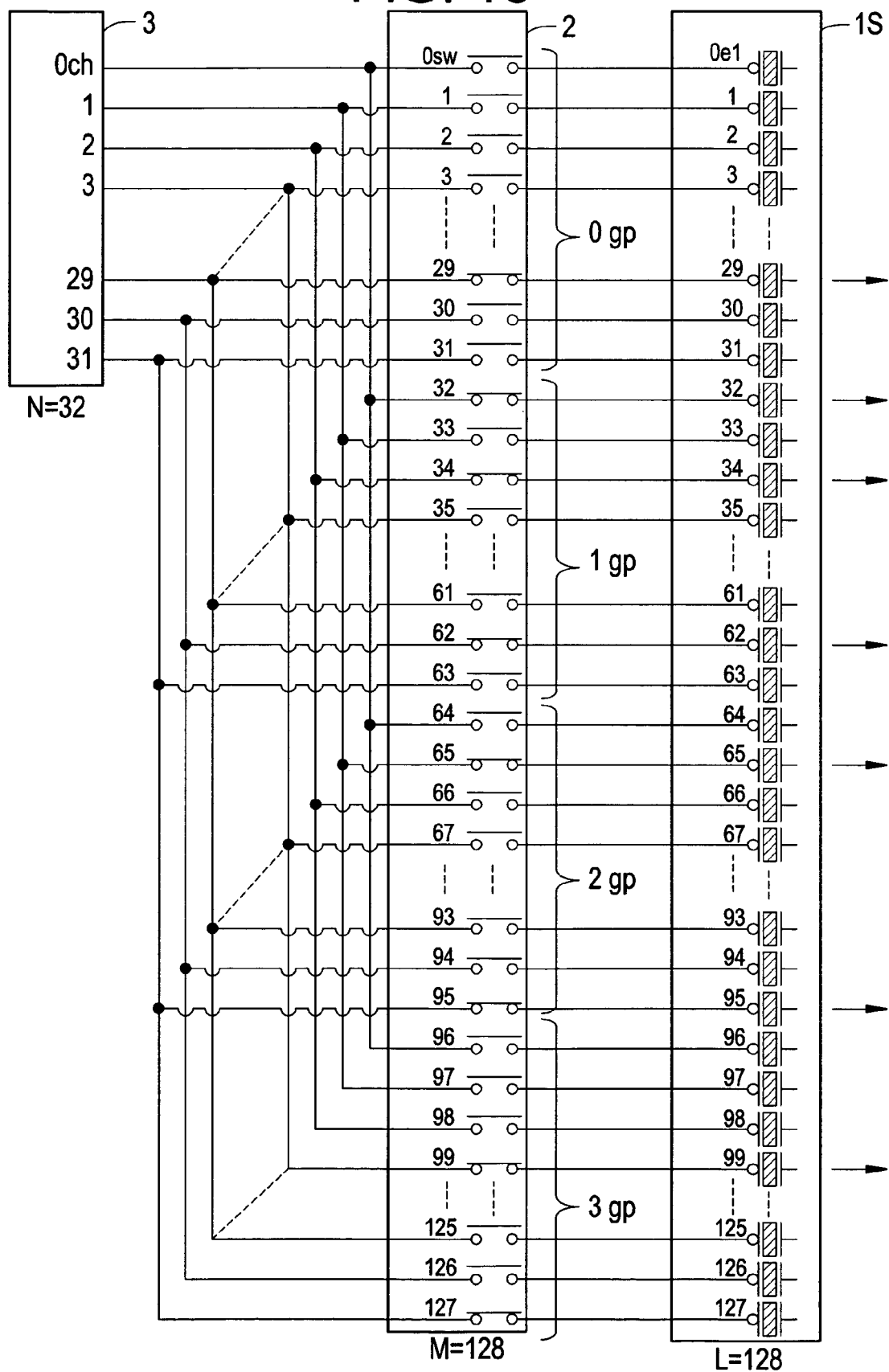
FIG. 16 is an explanatory diagram showing the connection among the sector probe, high voltage switch, and transmitter/receiver based on the sixth embodiment.

FIG. 16 is an explanatory diagram showing the connection among the sector probe 1S, high voltage switch 2, and transmitter/receiver 3 of a sixth embodiment. The parameters are set to be N=32, M=128 and L=128 in this embodiment.

Each n-th channel, where n takes 0 through 31, is connected in parallel fashion to the n-th switch, the (n+32)th switch, . . . , and the (n+96)th switch.

The sector probe 1S has its 0th through 127th vibration elements connected to the 0th through 127th switches, respectively.

Each set of a m-th through (m+31)th switches, where m takes 0, 32, 64 and 96), are united to be a (m/32)th switch group.

The controller 9 selects, out of the 0th through 63rd switches, 16 vibration elements which are located at random and are not connected to same channels, and turns on these 16 switches only. At this time, switches corresponding to vibration elements which are located at the middle or nearly middle of the alignment of vibration elements are selected at higher probabilities than probabilities of selection of switches corresponding to vibration elements which are located far from the middle of the alignment of vibration elements. Among the switches corresponding to the vibration elements which are located far from the middle of the alignment of vibration elements, odd-numbered switches are selected at high probabilities than probabilities of selection of even-numbered switches. Next, the controller 9 selects, out of the 64th through 127th switches, 16 switches which correspond to vibration elements located symmetrically or nearly symmetrically to the vibration elements which correspond to the turned-on switches among the 0th through 63rd switches across the middle of the alignment of vibration elements and are not connected to same channels and to the channels used by the turned-on switches among the 0th through 63rd switches, and turns on only these 16 switches. Consequently, only 32 vibration elements which are distributed at random in a half of the alignment of vibration elements and distributed virtually symmetrically in the middle of the alignment of vibration elements are driven.

Figure 17:
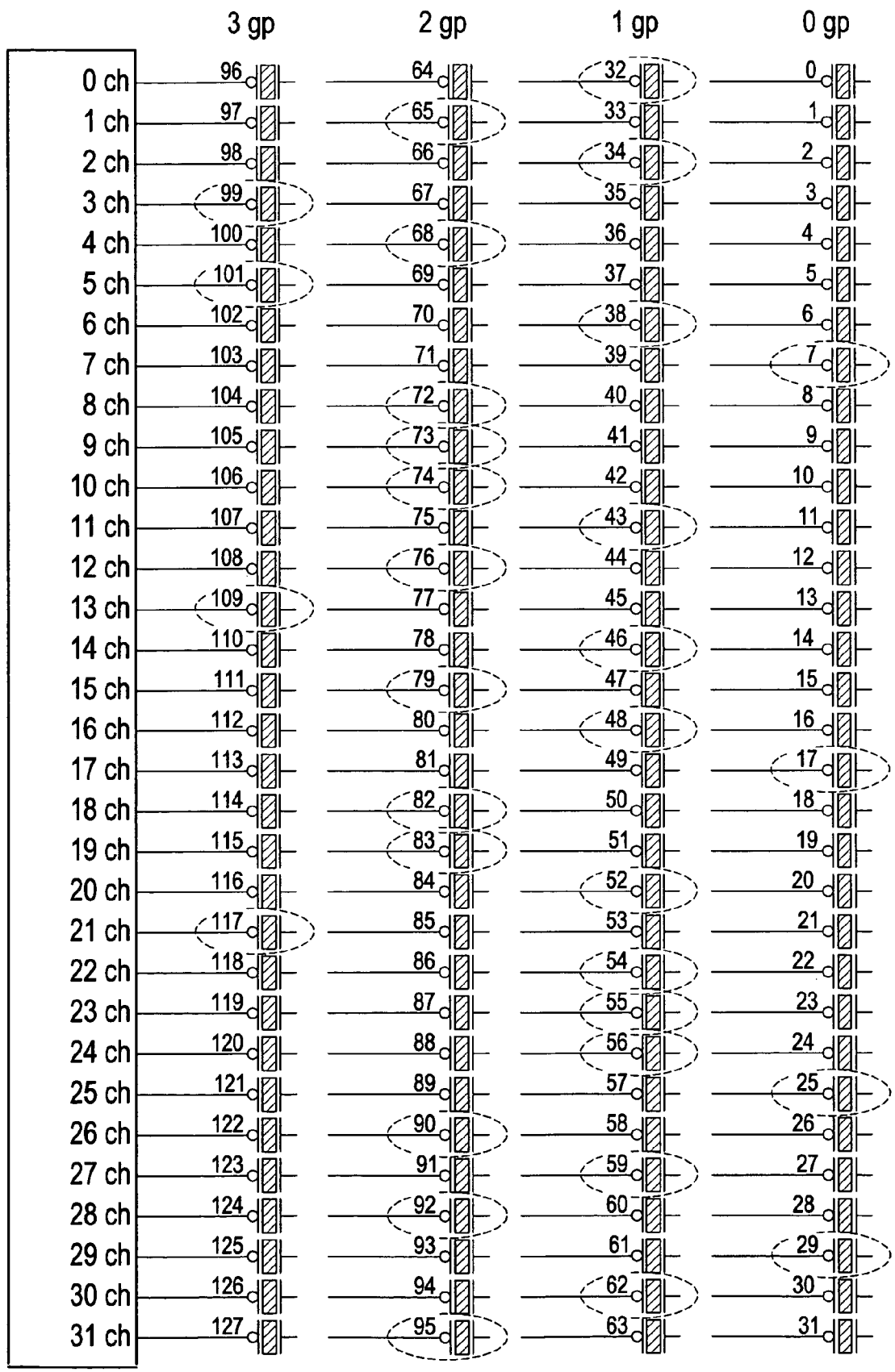
FIG. 17 is an explanatory diagram showing the correspondence between the channels of the transmitter/receiver and the vibration elements of the sector probe based on the sixth embodiment.

FIG. 17 is an explanatory diagram showing the correspondence between the channels of the transmitter/receiver 3 and the vibration elements of the sector probe 1S of the sixth embodiment. Vibration elements to be driven are marked by dashed ellipsoids.

FIG. 17 reveals that four vibration elements are selected at random out of the odd-numbered vibration elements of the 0th switch group, 12 vibration elements are selected at random out of the vibration elements of the 1st switch group, and only the switches corresponding to these vibration elements are turned on to drive the corresponding vibration elements. Out of the switches of the 2nd switch group, switches which correspond to vibration elements located symmetrically or nearly symmetrically to the vibration elements which correspond to the turned-on switches of the 1st switch group are selected, and only these switches are turned on. Out of the switches of the 3rd switch group, switches which correspond to vibration elements located symmetrically or nearly symmetrically to the vibration elements which correspond to the turned-on switches of the 0th switch group are selected, and only these switches are turned on. The vibration elements corresponding to these switches are driven.

As shown in FIG. 17, selective driving of 32 vibration elements, which are distributed at random (on condition that the distribution is more dense as the position is nearer to the middle) in a half of the alignment of vibration elements and distributed virtually symmetrically in the middle of the alignment of vibration elements, enables the sector scanning by use of the sector probe 1S. Based on the dense distribution of vibration elements to be driven in the middle section of the alignment of vibration elements and the distribution of vibration elements to reach the ends of the alignment of vibration elements so that the aperture can be fairly large, the sixth embodiment is useful without problems for any imaging mode.

Seventh Embodiment

Figure 18:
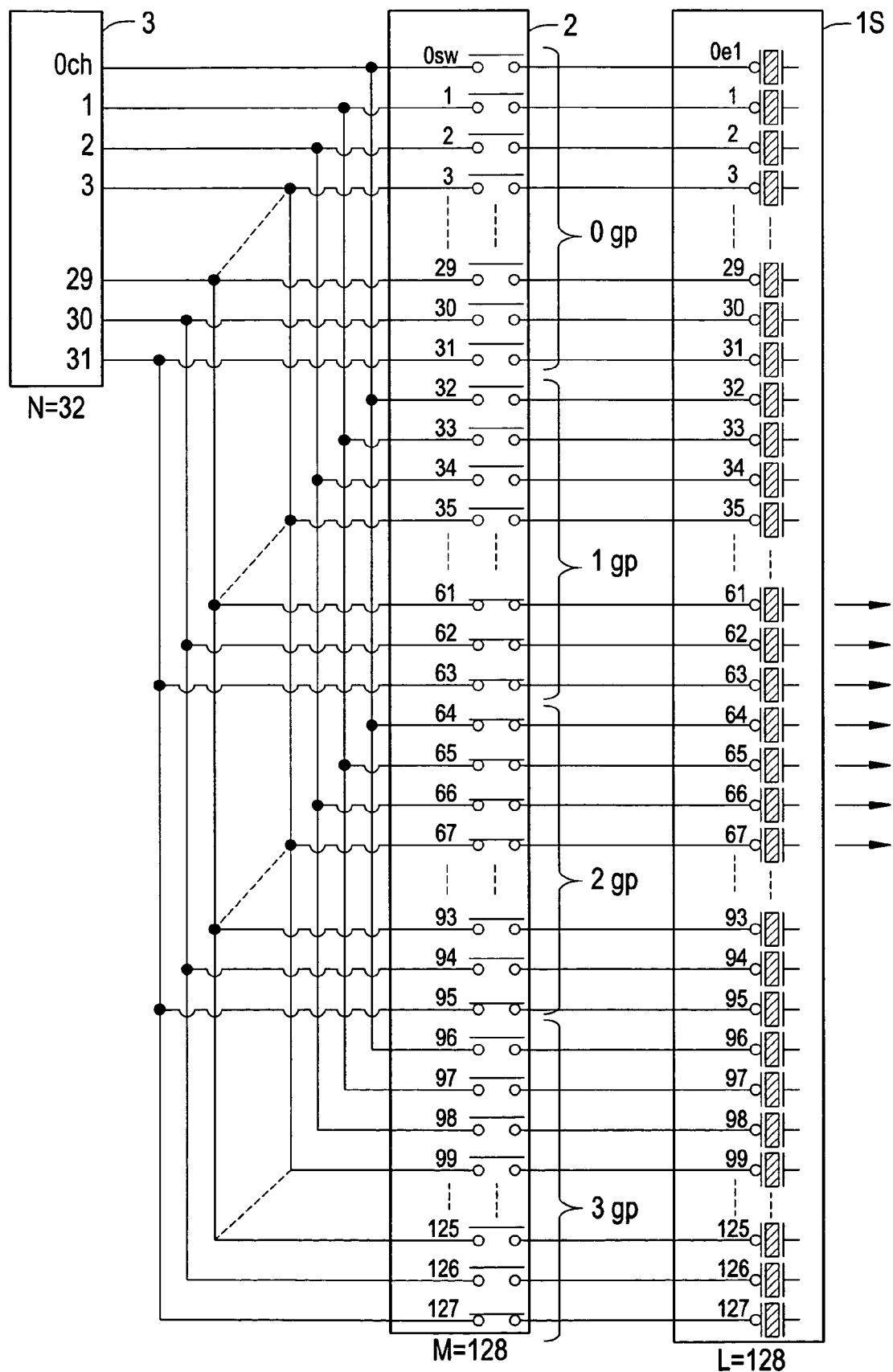
FIG. 18 is an explanatory diagram showing the connection among the sector probe, high voltage switch, and transmitter/receiver based on the seventh embodiment.

FIG. 18 is an explanatory diagram showing the connection among the sector probe 1S, high voltage switch 2, and transmitter/receiver 3 of a seventh embodiment. The parameters are set to be N=32, M=128 and L=128 in this embodiment.

Each n-th channel, where n takes 0 through 31, is connected in parallel fashion to the n-th switch, the (n+32)th switch, . . . , and the (n+96)th switch.

The sector probe 1S has its 0th through 127th vibration elements connected to the 0th through 127th switches, respectively.

The controller 9 turns on the 56th through 71st switches, turns on every second of the 40th through 54th switches, turns on every second of the 73rd through 87th switches, and turns off other switches which are connected to vibration elements. Consequently, 16 contiguous vibration elements located at the middle or nearly middle of the alignment of vibration elements and every second of 16 vibration elements located on both sides of these middle elements only are driven.

Figure 19:
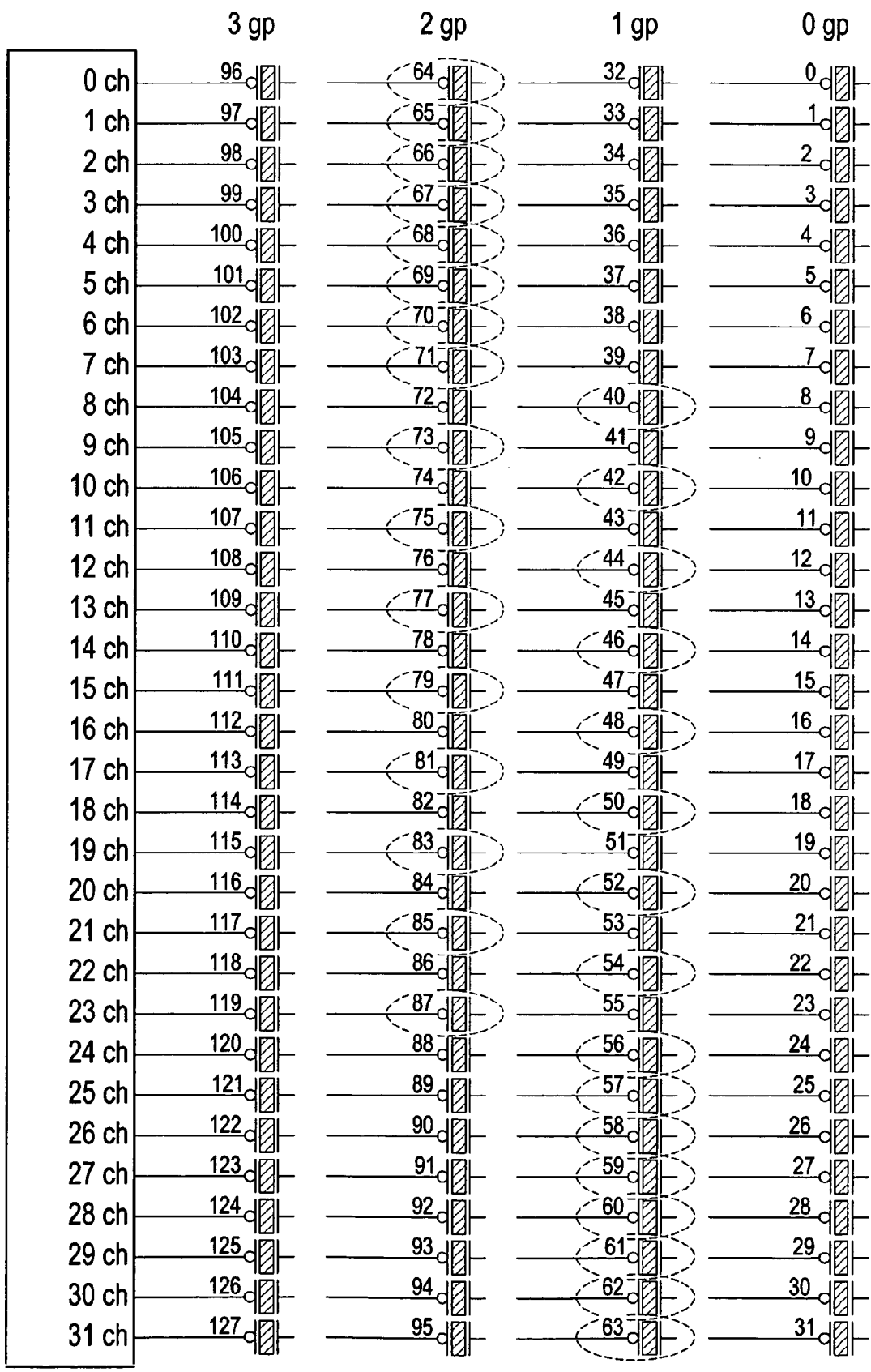
FIG. 19 is an explanatory diagram showing the correspondence between the channels of the transmitter/receiver and the vibration elements of the sector probe based on the seventh embodiment.

FIG. 19 is an explanatory diagram showing the correspondence between the channels of the transmitter/receiver 3 and the vibration elements of the sector probe 1S of the seventh embodiment. Vibration elements to be driven are marked by dashed ellipsoids.

FIG. 19 reveals that 16 contiguous vibration elements located at the middle or nearly middle of the alignment of vibration elements and every second of 16 vibration elements located on both sides of these middle elements only are driven.

As shown in FIG. 19, based on a dense distribution of vibration elements to be driven in the middle section of the alignment of vibration elements and the provision of a fairly large aperture, the seventh embodiment is useful for any imaging mode without significant problems.

Eighth Embodiment

It is preferable to make operative at least two of the first through seventh embodiments and carry out one of the two embodiments based on the selection by the controller 9 or the operator depending on at least one of the ultrasound diagnostic mode, scanning depth, scanning angle, and ultrasound frequency.

Other Embodiments

Although the foregoing embodiments are on the assumption that the transmitter and receiver have equally N channels, the present invention can be applied to cases where the transmitter and receiver have different numbers of channels. Specifically, the invention is applied by putting the number of channels of the transmitter to N, and, independently of this, the invention is applied by putting the number of channels of the receiver to N.

Many widely different embodiments of the invention may be configured without departing from the spirit and the scope of the present invention. It should be understood that the present invention is not limited to the specific embodiments described in the specification, except as defined in the appended claims.

The invention claimed is:

1. A method of driving a sector probe using a system comprising a transmitter/receiver for a convex probe and a linear probe, the transmitter/receiver having N number of channels, the sector probe having vibration elements of L in number, wherein L is larger than N, said method comprising:
coupling the transmitter/receiver to a switch system including M number of switches corresponding to M number of vibration elements in at least one of the convex probe and the linear probe, wherein M is larger than N;
coupling the sector probe to the switch system;
selecting (N/2) number of vibration elements at random out of a first switch group including (L/2) switches;
selecting (N/2) number of vibration elements out of a second switch group including (L/2) switches, the selected (N/2) number of vibration elements of the second switch group are nearly symmetrical to the (N/2) number of vibration elements selected at random out of the first switch group including (L/2) switches; and
driving the selected (N/2) vibration elements.

2. A sector probe driving method according to claim 1, wherein the probability of selection of vibration elements which are located at the middle or nearly middle of the alignment of vibration elements is raised.

3. A sector probe driving method according to claim 1, wherein the probability of selection in contiguous order of vibration elements which are located far from the middle of the alignment of vibration elements is lowered.

4. A sector probe driving method according to claim 1, further comprising dividing the M number of switches into a plurality of switch sub-groups each having (M/N) number of switches.

5. A sector probe driving method according to claim 1, wherein coupling the sector probe to the switch system further comprises coupling a sector probe to the switch system, the sector probe comprising L number of elements, wherein L is equal to M number of elements of at least one of the convex probe and the linear probe.

6. A sector probe driving method according to claim 1, wherein coupling the sector probe to the switch system further comprises coupling a sector probe to the switch system, the sector probe comprising L number of elements, wherein L number of elements of the sector probe is less than M number of elements of at least one of the convex probe and the linear probe.

7. An ultrasound diagnostic apparatus comprising:
a transmitter or a receiver for at least one of a convex probe and a linear probe, the transmitter or the receiver having 0th through (N−1)th channels;
a high voltage switch including 0th through (M−1)th switches, wherein M has a value of N multiplied by a natural number k of 2 or larger, and wherein M is equal to a number of vibration elements of at least one of the convex probe and the linear probe; and
a sector probe having vibration elements of L in number, wherein which are aligned in the order from the 0th through (L−1)th vibration elements,
each n-th channel, wherein n takes 0 through N−1, being connected in parallel fashion to the n-th switch, the (n+N)th switch, . . . , and the (n+(k−1)N)th switch,
the 0th through (L−1)th vibration elements of the sector probe being connected to the 0th through (L−1)th switches, respectively,
each set of m-th through (m+N−1)th switches, wherein m takes 0, N, . . . , (k−1)N, being united to be a (m/N)th switch group,
said ultrasound diagnostic apparatus further comprising:
a switch control device which selects at least two switch groups in which all switches are connected with vibration elements, turns on only odd-numbered switches for a first switch group, turns on only even-numbered switches for a second switch group, and turns off switches which are of other switch groups and connected with vibration elements.

8. An ultrasound diagnostic apparatus according to claim 7, wherein said switch control device selects at least four switch sub-groups such that all switches are connected with vibration elements, said switch control device turns on only odd-numbered switches for a first switch sub-group and a third switch sub-group, and turns on only even-numbered switches for a second switch sub-group and a fourth switch sub-group.

9. An ultrasound diagnostic apparatus comprising:
a transmitter or a receiver for at least one of a convex probe and a linear probe, the transmitter or the receiver having 0th through (N−1)th channels;
a high voltage switch including 0th through (M−1)th switches, wherein M has a value of N multiplied by a natural number k of 2 or larger, and wherein M number of switches is equal to a number of vibration elements of at least one of said convex probe and said linear probe; and
a sector probe having vibration elements of L in number, wherein N<L≦M, which are aligned in the order from the 0th through (L−1)th vibration elements,
each n-th channel, wherein n takes 0 through N−1, being connected in parallel fashion to the n-th switch, the (n+N)th switch, . . . , and the (n+(k−1)N)th switch,
the 0th through (L−1)th vibration elements of the sector probe being connected to the 0th through (L−1)th switches, respectively,
said ultrasound diagnostic apparatus further comprising:
a switch control device which selects, out of the 0th through (L−1)th switches, vibration elements of N in number which are located at random and are not connected to same channels, turns on the N switches only, and turns off other switches which are connected with vibration elements.

10. An ultrasound diagnostic apparatus according to claim 9, wherein said switch control device selects switches which correspond to vibration elements located at the middle or nearly middle of the alignment of vibration elements at higher probabilities than probabilities of selection of switches which correspond to vibration elements located far from the middle of the alignment of vibration elements.

11. An ultrasound diagnostic apparatus according to claim 9, wherein said switch control device selects, out of switches corresponding to vibration elements which are located far from the middle of the alignment of vibration elements, one set of odd-numbered switches or even-numbered switches at higher probabilities than probabilities of selection of another set of switches.

12. An ultrasound diagnostic apparatus according to claim 9, wherein said (M−1) number of switches are divided into a plurality of switch sub-groups each having (M/N) number of switches.

13. An ultrasound diagnostic apparatus according to claim 9, wherein said switch control device selects (N/2) number of switches at random out of a first switch group including (L/2) switches, and selects (N/2) number of switches at random out of a second switch group including (L/2) switches.

14. An ultrasound diagnostic apparatus according to claim 9, wherein said switch control device selects (N/4) number of switches at random out of a first switch sub-group including (L/4) switches, selects (N/4) number of switches at random out of a second switch sub-group including (L/4) switches, selects (N/4) number of switches at random out of a third switch sub-group including (L/4) switches, and selects (N/4) number of switches at random out of a fourth switch sub-group including (L/4) switches.

15. An ultrasound diagnostic apparatus according to claim 14, wherein the first switch group comprises the first switch sub-group and the second switch sub-group, and the second switch group comprises the third switch sub-group and the fourth switch sub-group, said switch control device selects a plurality of odd-numbered switches from the first switch sub-group and a remainder of switches at random from the second switch sub-group, and selects a plurality of switches from the third switch sub-group that are located substantially symmetrically to a respective switch from the second switch sub-group and a plurality of switches from the fourth switch sub-group that are located substantially symmetrically to a respective switch from the first switch sub-group, wherein symmetry is determined substantially about a switch array middle.

16. An ultrasound diagnostic apparatus according to claim 9, wherein said switch control device selects switches from the first switch group based on a probability of selection of vibration elements weighted in favor of selecting a vibration element located at substantially a middle of an alignment of the vibration elements.

17. An ultrasound diagnostic apparatus according to claim 9, wherein said switch control device selects switches from the second switch group based on a probability of selection of switches weighted in favor of selecting a switch located substantially symmetrically to a switch selected from the first switch group, wherein symmetry is determined substantially about a switch array middle.

18. A sector probe driving method according to claim 1, wherein selecting (N/2) number of vibration elements at random out of a first switch group including (L/2) switches and selecting (N/2) number of vibration elements at random out of a second switch group including (L/2) switches further comprises:
- selecting vibration elements of (N/4) in number at random out of a first vibration element sub-group including (L/4) vibration elements;
- selecting vibration elements of (N/4) in number at random out of a second vibration element sub-group including (L/4) vibration elements;
- selecting vibration elements of (N/4) in number at random out of a third vibration element sub-group including (L/4) vibration elements; and
- selecting vibration elements of (N/4) in number at random out of a fourth vibration element sub-group including (L/4) vibration elements.

19. A sector probe driving method according to claim 18, wherein selecting vibration elements of (N/4) in number at random out of a first vibration element sub-group including (L/4) vibration elements and selecting vibration elements of (N/4) in number at random out of a second vibration element sub-group including (L/4) vibration elements further comprises selecting the vibration elements based on a probability of selection of vibration elements weighted in favor of selecting a vibration element located substantially at a middle of an alignment of the vibration elements.

20. A sector probe driving method according to claim 18, wherein selecting vibration elements of (N/4) in number at random out of a third vibration element sub-group including (L/4) vibration elements and selecting vibration elements of (N/4) in number at random out of a fourth vibration element sub-group including (L/4) vibration elements further comprises selecting the vibration elements based on a probability of selection of vibration elements weighted in favor of selecting a vibration element located substantially symmetrically to an element selected from at least one of the first vibration element sub-group and the second vibration element sub-group, wherein symmetry is determined substantially about an element alignment middle.

* * * * *